United States Patent
Kohlbrenner et al.

(10) Patent No.: US 10,300,211 B2
(45) Date of Patent: May 28, 2019

(54) INJECTION DEVICE COMPRISING AN IMPROVED DELIVERY ELEMENT

(71) Applicant: TecPharma Licensing AG, Burgdorf (CH)

(72) Inventors: Philippe Kohlbrenner, Kaltacker (CH); Peter Stettler, Kirchberg (CH); Patrick Hostettler, Hasle-Ruegsau (CH); Juergen Wittmann, Burgdorf (CH); Martin Wittwer, Wyssachen (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 16/119,307

(22) Filed: Aug. 31, 2018

(65) Prior Publication Data

US 2019/0022332 A1    Jan. 24, 2019

Related U.S. Application Data

(63) Continuation of application No. 15/336,156, filed on Oct. 27, 2016, which is a continuation of application
(Continued)

(30) Foreign Application Priority Data

Sep. 15, 2006   (CH) ........................... 1475/06

(51) Int. Cl.
   *A61M 5/315*   (2006.01)
   *A61M 5/24*    (2006.01)
   *A61M 5/20*    (2006.01)

(52) U.S. Cl.
   CPC .......... *A61M 5/31585* (2013.01); *A61M 5/20* (2013.01); *A61M 5/24* (2013.01);
   (Continued)

(58) Field of Classification Search
   CPC .......... A61M 5/31585; A61M 5/31513; A61M 5/31583; A61M 5/31553; A61M 5/20;
   (Continued)

(56) References Cited

U.S. PATENT DOCUMENTS

| | | |
|---|---|---|
| 2,771,217 A | 11/1956 | Brown et al. |
| 3,202,151 A | 8/1965 | Kath |

(Continued)

FOREIGN PATENT DOCUMENTS

| | | |
|---|---|---|
| CH | 617857 A5 | 6/1980 |
| DE | 10229122 A1 | 2/2004 |

(Continued)

*Primary Examiner* — Rebecca E Eisenberg
*Assistant Examiner* — Anh Bui
(74) *Attorney, Agent, or Firm* — Dorsey & Whitney LLP

(57) ABSTRACT

An injection device having a delivery element with an inner thread may be driven by rotation and includes a cylindrical outer wall region, which is substantially smooth. Such features provide a delivery element configured such that it is less intimidating to patients than known threaded rods, and may facilitate easy cleaning. The delivery element may be non-rotatably guided and axially spring-loaded, and may be inserted axially into the housing when the reservoir is replaced. The driving thread element for the delivery element may be mounted in the vicinity of the distal end of the housing.

20 Claims, 20 Drawing Sheets

Related U.S. Application Data

No. 14/455,243, filed on Aug. 8, 2014, now abandoned, which is a continuation of application No. 12/403,775, filed on Mar. 13, 2009, now Pat. No. 8,834,431, which is a continuation of application No. PCT/CH2007/000241, filed on May 11, 2007.

(52) U.S. Cl.
CPC .... *A61M 5/31513* (2013.01); *A61M 5/31553* (2013.01); *A61M 5/31561* (2013.01); *A61M 5/31583* (2013.01); *A61M 5/31593* (2013.01); *A61M 5/31535* (2013.01); *A61M 5/31541* (2013.01); *A61M 5/31543* (2013.01); *A61M 5/31563* (2013.01); *A61M 5/31568* (2013.01); *A61M 2005/202* (2013.01); *A61M 2005/3154* (2013.01); *A61M 2202/04* (2013.01); *A61M 2205/581* (2013.01)

(58) Field of Classification Search
CPC ................ A61M 5/31543; A61M 5/24; A61M 5/31535; A61M 5/31541; A61M 5/31551; A61M 5/31568; A61M 2005/2407; A61M 2005/2403; A61M 2005/2411; A61M 2005/3154

See application file for complete search history.

(56) References Cited

U.S. PATENT DOCUMENTS

| | | |
|---|---|---|
| 5,049,125 A | 9/1991 | Accaries et al. |
| 5,514,097 A | 5/1996 | Knauer |
| 5,569,236 A | 10/1996 | Kriesel |
| 6,123,684 A | 9/2000 | Deboer et al. |
| 6,277,099 B1 | 8/2001 | Strowe et al. |
| 7,083,596 B2 | 8/2006 | Saied |
| 7,112,187 B2 | 9/2006 | Karlsson |
| 7,195,616 B2 | 3/2007 | Diller et al. |
| 7,645,265 B2 | 1/2010 | Stamp |
| 2005/0022806 A1 | 2/2005 | Beaumont et al. |
| 2005/0065477 A1 | 3/2005 | Jost |
| 2005/0080377 A1 | 4/2005 | Sadowski et al. |
| 2005/0197626 A1 | 9/2005 | Moberg et al. |
| 2005/0209570 A1 | 9/2005 | Moller |
| 2005/0261634 A1 | 11/2005 | Karlsson |
| 2006/0153693 A1 | 7/2006 | Fiechter et al. |
| 2006/0184117 A1 | 8/2006 | Knight et al. |
| 2006/0206057 A1 | 9/2006 | Deruntz et al. |
| 2007/0016143 A1 | 1/2007 | Miller et al. |
| 2007/0021715 A1 | 1/2007 | Kohlbrenner et al. |
| 2007/0027430 A1 | 2/2007 | Hommann |
| 2008/0033369 A1 | 2/2008 | Kohlbrenner et al. |
| 2008/0051712 A1 | 2/2008 | Fiechter et al. |
| 2008/0051713 A1 | 2/2008 | Kohlbrenner et al. |
| 2008/0171997 A1 | 7/2008 | Kohlbrenner et al. |
| 2008/0287883 A1 | 11/2008 | Radmer et al. |
| 2008/0306445 A1 | 12/2008 | Burren et al. |
| 2009/0048561 A1 | 2/2009 | Burren et al. |
| 2009/0247959 A1 | 10/2009 | Kohlbrenner et al. |
| 2009/0247960 A1 | 10/2009 | Kohlbrenner et al. |
| 2009/0254035 A1 | 10/2009 | Kohlbrenner et al. |
| 2009/0254044 A1 | 10/2009 | Kohlbrenner et al. |
| 2009/0299297 A1 | 12/2009 | Moeller et al. |

FOREIGN PATENT DOCUMENTS

| | | |
|---|---|---|
| DE | 102004063644 A1 | 7/2006 |
| DE | 102004063647 A1 | 7/2006 |
| EP | 0554995 A1 | 8/1993 |
| EP | 1681070 B1 | 2/2009 |
| EP | 1516638 B1 | 1/2010 |
| WO | 0041754 A1 | 7/2000 |
| WO | 0119434 A1 | 3/2001 |
| WO | 02053214 A1 | 7/2002 |
| WO | 2004002556 A1 | 1/2004 |
| WO | 2004089450 A1 | 10/2004 |
| WO | 2006039930 A1 | 4/2006 |
| WO | 2006130100 A1 | 12/2006 |

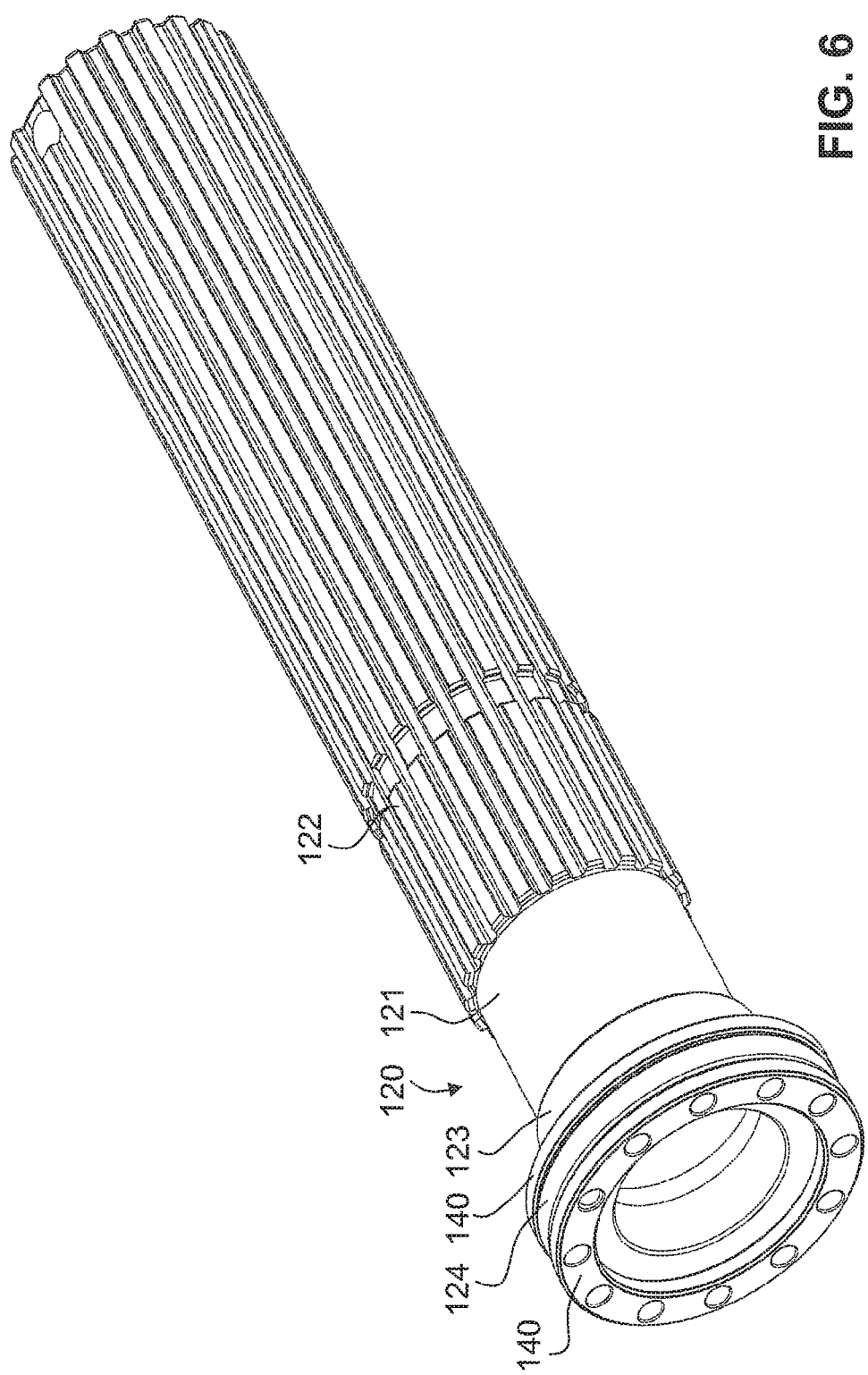

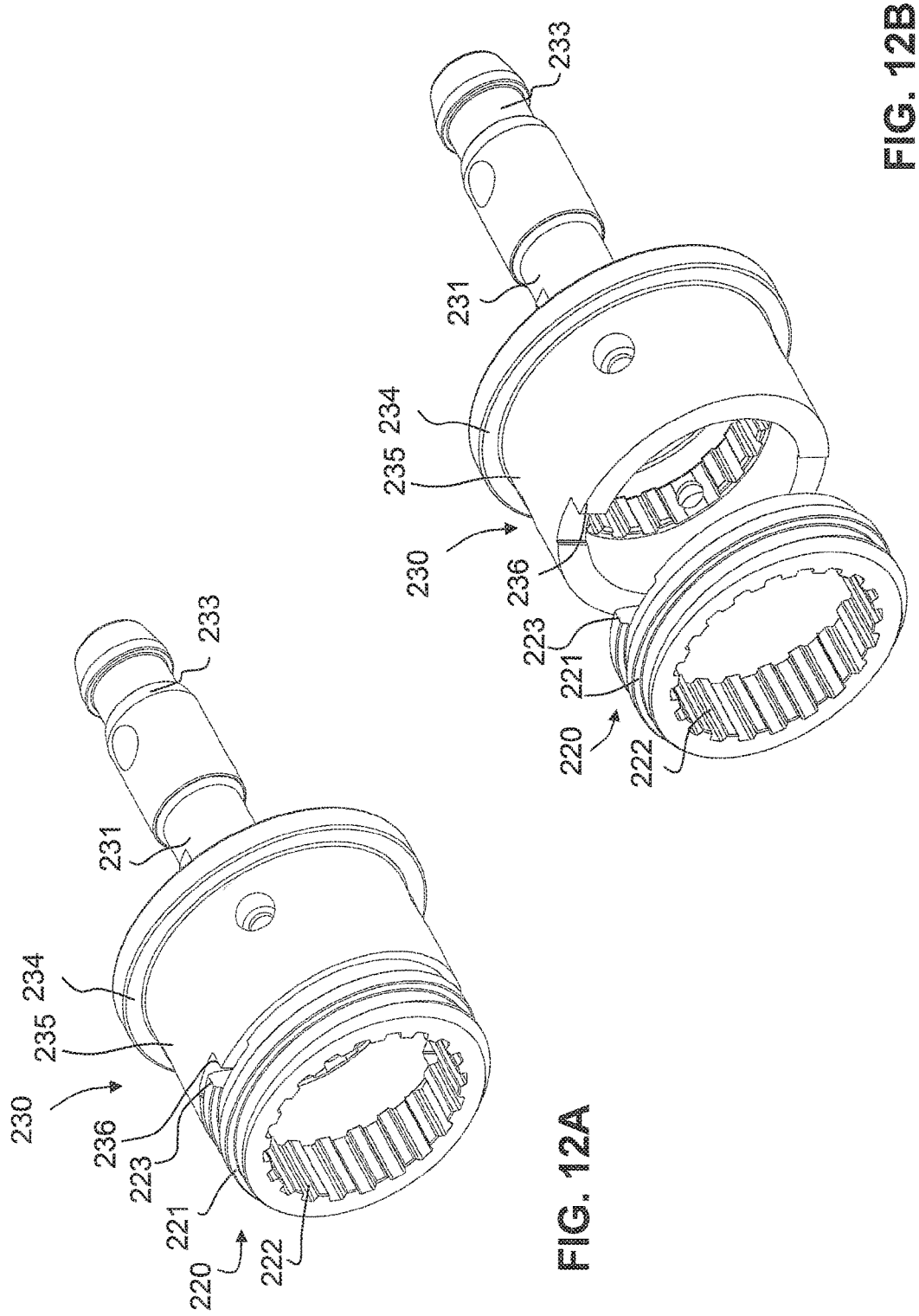

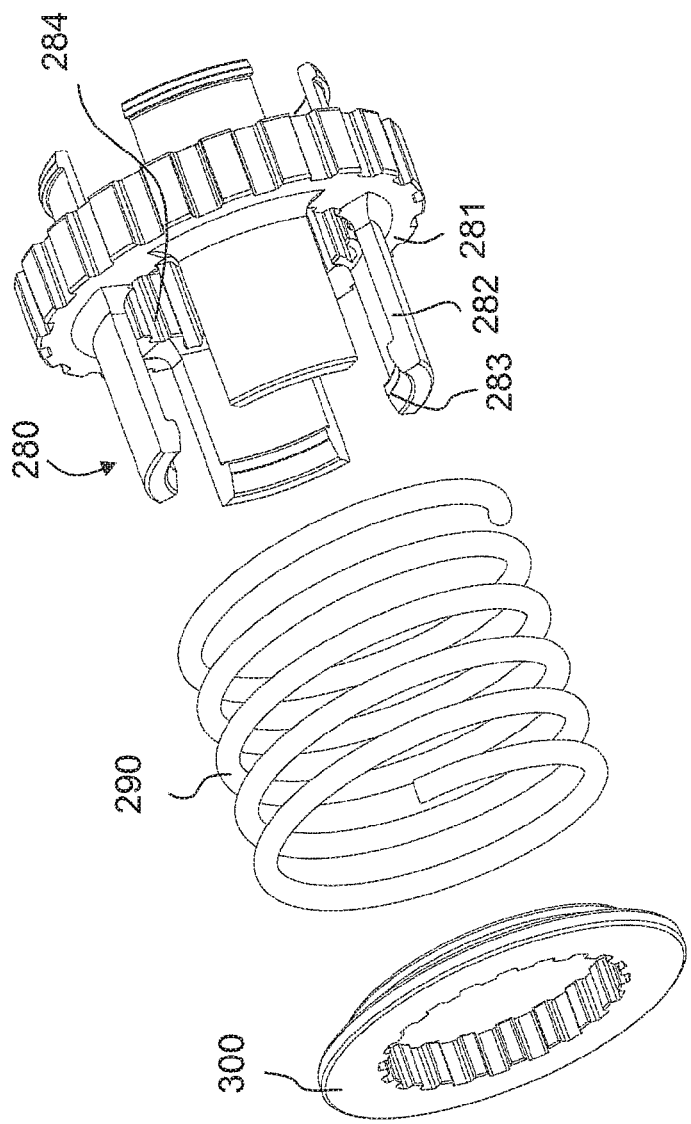

INJECTION DEVICE COMPRISING AN IMPROVED DELIVERY ELEMENT

CROSS-REFERENCE TO RELATED APPLICATIONS

This application is a continuation of U.S. patent application Ser. No. 15/336,156 filed Oct. 27, 2016, which is a continuation of U.S. patent application Ser. No. 14/455,243 filed Aug. 8, 2014 (abandoned), which is a continuation of U.S. patent application Ser. No. 12/403,775 filed Mar. 13, 2009, issued as U.S. Pat. No. 8,834,431 on Sep. 16, 2014, which is a continuation of International Patent Application No. PCT/CH2007/000241 filed May 11, 2007, which claims priority to Swiss Patent Application No. 1475/06 filed Sep. 15, 2006, the entire contents of both of which are incorporated herein by reference.

BACKGROUND

The present invention relates to devices for administering, injecting, delivering, infusing or dispensing a substance, and to methods of making and using such devices. More particularly, it relates to such a device for delivering a fluid product, wherein the device can be developed as an injection device for the injection of an adjustable dose of the product and can take the form of an injection pen, i.e. a compact injection device in pen-like form.

A large number of injection devices are known from the prior art for the dosed administering of medicaments or therapeutic agents such as insulin, growth hormones or osteoporosis drugs, which must be administered regularly. Such devices are on the one hand intended to reliably and precisely deliver a dose which is able to be pre-set. On the other hand, they are intended to be user-friendly to a high degree. This applies all the more because they are generally operated by a person for self-adminsitration.

The medicament can be housed in an exchangeable carpule (which also may be thought of and/or referred to as an ampoule, receptacle, container or reservoir), which is able to be inserted into a carpule holder. The latter can then be associated with or fastened to a housing of the injection device, e.g. by a screw connection or a bayonet connection. For distribution, a product stopper or piston in the carpule is pushed forward (toward the needle associated with the injection device) by a delivery arrangement with a delivery element in the form of a piston rod.

Compact, pen-shaped administering devices are known, in which the distribution takes place automatically after a first triggering (e.g. "power-assisted pens"). The dose in such devices is generally pre-set by a rotation of a dosing button. A drive is present in the device, e.g. a spring drive, which is tensioned on setting of the dose. The device is triggered by pressing a triggering arrangement, which can be identical to the dosing button. In so doing, the drive generates a drive movement, e.g. in the form of a rotary movement, which is converted into an advancing movement of the piston rod. In the case of a drive by a rotary movement, the piston rod may be constructed as a threaded rod on which a drive nut runs. Examples of such injection pens are disclosed in DE-A 10 2004 063 644, DE-A 10 2004 063 647, WO-A 2004/002556 and DE-A 102 29 122.

In EP-A 1 681 070, a manually driven injection pen is disclosed, wherein the piston rod is hollow and has an internal thread instead of an external thread. This internal thread is in engagement with the external thread of a rotatable drive shaft, which, in the region of its proximal end, is mounted opposite an inner housing part. The piston rod has on its outer side continuous longitudinal grooves into which projections of a fixing bush engage. This fixing bush is secured relative to the housing when a receptacle holder is connected with the housing, and can freely rotate when the receptacle holder is detached from the housing. On administering of a dose, the drive shaft rotates and thereby advances the piston rod linearly, which is guided to be locked against relative rotation via the fixing bush. In the case of a change of reservoir, the receptacle holder is detached from the housing. Thereby, the fixing bush, and with it also the piston rod, is freely rotatable with respect to the housing. When the piston rod is pushed into the housing, the drive shaft remains stationary and the piston rod performs a screw motion.

This device is capable of improvement in several respects. For example, the screw motion of the piston rod compulsorily requires, on insertion, that at its distal end a cap is rotatably mounted, which, on insertion, does not co-rotate with the piston rod, because otherwise on insertion no suitable counter-surface would be available which is locked against relative rotation, on which the axial force, required for insertion, could engage. Furthermore, the presence of the fixing bush requires that longitudinal grooves are formed on the outer side of the piston rod. Dirt can accumulate in these. Moreover, a bearing of the drive shaft relative to the housing in its proximal end region is disadvantageous, because a large amount of space is required for this in a region in which otherwise, for example, drive components could be housed. Also, in this device it is not ensured that the piston rod also actually touches the stopper of the medicament reservoir.

SUMMARY

In accordance with the present invention, and according to a first aspect of the presently disclosed embodiments, a device for administering a fluid product includes a housing and a delivery element for the delivery of the product from a reservoir. The delivery element is movable relative to the housing along a thrust axis. Instead of an external thread, the delivery element has an internal thread, the thread axis of which runs along the thrust axis. Thereby, the thread is used for the drive is not visible to the user, and the outer side of the delivery element may thus have a variety of configurations, and for example, may be adapted to the needs of the user and other technical requirements. In addition, a compact arrangement becomes possible. The device comprises a drive arrangement and a thread element with an external thread, which is in engagement with the internal thread of the delivery element, and may be fixed relative the housing along the thrust axis and may be set in a rotary movement about the thrust axis by the drive arrangement to advance the delivery element along the thrust axis.

According to certain embodiments, the delivery element is guided so as to be locked against relative rotation with respect to the housing in a number of instances, and therefore performs a linear thrust movement both on the thrust movement for the ejection of the product and also on pushing back on the change of a receptacle.

In some embodiments, the thread element may be constructed as an external threaded rod, and the delivery element may include a short internal thread, compared with the external thread of the thread element, only in the region of its proximal end, to minimize friction losses.

In some embodiments, the delivery element may be spring-loaded in a distal (forward) direction, i.e., the direction in which the thrust takes place. The spring cooperating with the delivery element may be configured and arranged so as to not bring about an ejection of the product out of the reservoir. Rather, it serves, in the case of a reservoir change, to bring the delivery element automatically into its distal final position, i.e., to move it out completely, when the reservoir is removed from the housing. In this way, the delivery element may touch the reservoir stopper at all times. The corresponding spring may be housed in the interior of the thread element configured as a hollow spindle, may be configured as a helical spring, and may be guided on a guide needle.

In certain embodiments, the device includes a receptacle holder detachable from the housing to hold the reservoir with the product. In a state in which the receptacle holder is detached from the housing, the thread element may be rotatable with respect to the housing such that the delivery element is insertedable into the housing by an axial displacement in the proximal direction. Here, the thread element co-rotates forming a the threaded engagement with the delivery element.

In some embodiments, the delivery element is surrounded radially at least partially by a guide sleeve with a proximal and a distal end. The length of this guide sleeve may correspond at least to the maximum thrust range of the delivery element, i.e., the distance between the distal and the proximal (rearward) final position of the delivery element. Close to its distal end, the guide sleeve is connected, at least during the administering, so as to be locked against relative rotation with the housing or with an element fixed to the housing. The delivery element is guided along the thrust direction so as to be locked against relative rotation in the guide sleeve. For this, the delivery element, at least in the region of its proximal end, may be in an engagement, locked against relative rotation, with the interior of the guide sleeve, which engagement, however, permits an axial displacement. For this, in the region of the proximal (rear) end, an engagement structure, e.g., in the form of several longitudinal ribs, may be configured to project radially outward from the outer peripheral surface of the delivery element, cooperating with a complementary structure, e.g., in the form of several longitudinal grooves on the inner peripheral surface of the guide sleeve. The device may comprise, in addition, an outer sleeve with a proximal and a distal end, which, radially surrounds the guide sleeve at least partially. Close to its proximal end, this outer sleeve is connected with the rotatable element. Close to its distal end, the outer sleeve is rotatable and is guided so as to be secured with regard to displacement relative to the guide sleeve.

Accordingly, in the exemplary embodiments provided herein, the delivery element may be secured against rotation relative to the stationary housing and guided longitudinally. In some embodiments, the delivery element may be configured, on its outer side, with a substantially smooth surface. Thus the delivery element is guided longitudinally in the region of its proximal end in an element, which is locked against relative rotation with respect to the housing. However, such a configuration may require that the delivery element, which is locked against relative rotation, have a length such that the guiding is provided over the range of the thrust of the delivery element. Accordingly, a sleeve-like structure of the element, which is locked against relative rotation, is provided, which is therefore designated as a guide sleeve, with a length of this guide sleeve corresponding at least to the thrust range of the delivery element. To drive the delivery element, the rotatable element may be arranged inside the delivery element. To provide a thread or threaded engagement over the thrust range, the rotatable element may extend at least over a length of proximal to distal into the delivery element which corresponds to the thrust range. Access to the rotatable element, and in some embodiments, the one available access, may be provided here from the proximal end. A driving of the rotatable element may therefore take place over its proximal end. At the same time, the rotatable element may be mounted in any manner relative to an element which is fixed to the housing. This mounting absorbs axial forces, which are transmitted from the delivery element via the thread engagement to the rotatable element. A mounting may be provided directly at the proximal end of the rotatable element. However, this would take up a large amount of space in a region, which is to be available for other functions.

It therefore may be desirable to reposition the site of the bearing to another location, e.g., as close as possible to one of the ends of the housing. This may take place by using the outer sleeve, which is securely connected with the rotatable element and continues along the outer side of the guide sleeve towards the distal direction. Mounting is provided between the outer sleeve and the guide sleeve, and namely in the region of the distal (forward) end of the outer sleeve. As a result, a compact unit may be provided, the mounting of which, taking up a relatively large amount of space radially, comes to lie in a proximal (rear) region, thus enabling the injection device to accommodate further elements in the radial intermediate space between the outer sleeve and the housing. Furthermore, because the outer sleeve (and thus the rotatable element) is mounted on the guide sleeve and not, for instance, on the housing itself, the guide sleeve, outer sleeve, mounting, rotatable element and delivery element may be formed as a unit, and may be movable systematically with respect to the housing, e.g., in the changeover of a receptacle.

According to further embodiments, an injection device for the administering of a fluid product in accordance with the present invention comprises a housing and a delivery element for the delivery of the product from a reservoir. The delivery element is movable relative to the housing along a thrust axis between a proximal (rearward) initial position and a distal (forward) final position, and may be guided so as to be locked against relative rotation. The delivery element may project through a passage opening in a boundary wall of the housing. A drive arrangement may be configured for producing a rotary movement of a rotatable element relative to the housing, wherein the rotatable element is coupled with the delivery element so that the rotary movement brings about a thrust movement of the delivery element along the thrust axis. The delivery element may have a substantially smooth outer wall region, the length of which corresponds at least to the distance between the distal final position and the proximal initial position. In this way, it becomes possible to arrange the delivery element so that during the thrust, the smooth outer wall region is advanced through the opening in the housing wall. Thus, viewing an external thread, which could have a deterrent effect on the user may be avoided. Also, the need to clean a thread or threading is avoided or at least minimized.

A "substantially smooth" outer wall region is a region of the outer peripheral surface of the delivery element, that does not have any technically necessary structures (except as otherwise indicated), e.g., no structures such as threads, deep relieved regions, highly raised regions or grooves are present, which could lead to an insufficient acceptance by the user or could make cleaning difficult. On the other hand, however, the outer wall region may be configured, for example, with fine structures like micro- or nano-structuring. Distally from the smooth outer wall region, for example, a structure may adjoin, which is configured to advance a stopper in the product container, e.g., a thrust flange projecting radially over the outer wall region. The region arranged proximally from the outer wall region, on the other hand, is normally situated permanently inside the housing and is therefore invisible to the user. This proximal region may therefore be provided with a configuration as desired or that meets technical requirements.

If the thrust of the delivery element is to take place via an external thread on which a drive nut runs in a conventional manner, then this external thread may adjoin the smooth outer wall region proximally.

In some embodiments, the delivery element is sealed so as to be fluid-tight, at least protected against splash water, with respect to the housing or to an element fixed to the housing. Thereby, a penetration of fluids may be prevented.

A corresponding seal may be constructed directly between the delivery element and the housing. However, a first seal may be constructed between the delivery element and an element that is movable relative to the housing, and a second seal is constructed between the movable element and the housing. The movable element may be arranged, for example, so that it is movable when the reservoir is being changed, and is immovable with respect to the housing during the actual administering. It may be cylindrical or sleeve-shaped.

In some embodiments, a substantially smooth, cylindrical, e.g., circular cylindrical, outer wall region is surrounded by at least one ring-shaped sealing element. In this way, a sealing may be achieved, as is not possible in the case of other known piston rods with external threading, which would oppose or interfere with an efficient sealing effect. As presently proposed, the length of the substantially smooth outer wall region, e.g., without structures such as threads or grooves, corresponds at least to the distance between the distal final position and the proximal initial position, between which the delivery element is moveable in the course of the administering, to provide a sealing over this entire region. The outer wall region may have fine structures, e.g. scales, a pattern or texture, in the range below 100 micrometers, e.g., below 10 micrometers, which are suited to at least not impair the sealing effect, or may improve it, e.g., a micro- or nano-structuring. These structures may have a selected direction to inhibit a flow of fluids.

In some embodiments, the at least one ring-shaped sealing element comprises at least one circumferential, flexible sealing lip, which rests on the cylindrical outer wall region and acts in the manner of a windscreen wiper as a stripper. The contact angle between the sealing lip and the outer wall region may be to less than 90 degrees. However, it can also be constructed for example as a ring with a round or polygonal cross-section.

In some embodiments, the interior of the housing may be sealed in a fluid-tight manner with respect to the exterior of the housing, i.e., not only in the region in which the delivery element is guided outwards, but also in other regions, e.g., in the region of movable dosing or actuating elements.

In some embodiments, the delivery element or an element cooperating therewith in a sealing manner may be composed of a hydrophobic material or may be coated hydrophobically, in order to achieve or improve a sealing effect, thus avoiding a creeping due to a capillary effect.

In some embodiments, the reservoir may be held in a receptacle holder, and may be fastened to the housing in a detachable manner. On fastening, this receptacle holder is guided with respect to the housing such that, relative to the housing, it carries out a combined rotary movement about a rotation axis and a translation movement along the rotation axis. The device may further comprise a spring element and a detent element. These elements may be arranged such that the spring element produces a spring force onto the detent element acting substantially along the rotation axis. The detent element thereby brings about in a predetermined holding position of the receptacle holder, a detachable detent connection, by which the receptacle holder is fixed relative to the housing. For example, a projection of the detent element can project into a depression of the receptacle holder or of an element, which is locked against relative rotation with respect thereto. A reverse arrangement is also conceivable. The detent connection may be configured so that it is able to be detached through a movement of the receptacle holder relative to the housing, which is opposed to the movement on fastening, i.e., the detent connection does not need to be unlocked manually.

Therefore, a connection in the manner of a screw or bayonet connection is provided between the receptacle holder and the housing or between elements connected with these. In conventional bayonet connections between two elements, an element with a bayonet pin is guided in a suitably formed slit or in a corresponding groove in the manner of a connecting link guide of the other element, until the bayonet pin reaches a final position (corresponding to the holding position). In such connections, an unintentional sliding back of the pin out of the final position may be a problem. A similar problem also occurs in screw connections, which are fixed by a clamping force and which may similarly become detached unintentionally. The device presented herein addresses this problem by providing, in some preferred embodiments, an axially spring-loaded (and axially movable) detent element. Such a detent element provides a defined fixing of the receptacle holder in the holding position, without the risk of an unintentional detachment. The connection may be detachable again by overcoming a sufficiently great force. Here, an abrasion, which could lead to a wearing out of the connection, is avoided. By the detent element being spring-loaded into the axial direction, the detent element and the spring element provide for space-savings.

The receptacle may be a container with a cylindrical wall region and with a stopper displaceable therein, e.g., a carpule, which defines a longitudinal direction and is housed in a receptacle holder with a correspondingly elongated form. When fastening on the housing, the receptacle holder may be rotated about this longitudinal direction, i.e., the rotation axis coincides with the longitudinal axis. For the administering of the product, the stopper is advanced by the delivery element along the longitudinal direction. That is, the thrust direction of the delivery element corresponds to a direction along the rotation axis about which the receptacle holder is rotated during its fastening.

The arrangement of the spring and detent element may be provided with a variety of configurations. According to a certain embodiments, the detent element is locked against relative rotation with respect to the housing, and in the detent position, it is detachably engaged with an element which is locked against relative rotation with respect to the receptacle holder. In other words, the detent element does not follow the rotation of the receptacle holder, but remains locked against relative rotation with respect to the housing on fastening of the receptacle holder. However, the reverse arrangement is also conceivable, in which the detent element is locked against relative rotation with respect to the receptacle holder.

In various embodiments, the device comprises a carrier element, which is rotatably arranged relative to the housing. The carrier element is guided with respect to the housing such that, on fastening of the receptacle holder on the housing and on detaching the receptacle holder from the housing, it is entrained by the receptacle holder and is set into a movement, which comprises a rotary movement about the rotation axis. In the holding position of the receptacle holder, the detent element brings about a detachable detent connection, by which the carrier element is fixed relative to the housing. This, in turn, holds the receptacle holder. The receptacle holder is therefore fixed indirectly, via the carrier element, relative to the housing. Thereby, a greater freedom is made possible in the design of the receptacle holder and of the detent element and spring element.

In some embodiments of the present invention, an injection device also comprises a guide element arranged so as to be locked against relative rotation with respect to the housing, which guide element can be constructed as a guide sleeve. This guide element can be rigidly connected with the housing, can be configured integrally therewith, or it can be displaceable axially with respect to the housing. The carrier element, which can likewise be formed as a sleeve, and can then be designated as a bayonet sleeve, is connected at least rotatably with the guide element. The spring element and the detent element may be arranged so as to be locked against relative rotation with respect to the guide element, and in the holding position of the receptacle holder, the detent element is engaged detachably with the carrier element. For example, the guide element may be connected so as to be axially displaceable with respect to the housing and the carrier element may be connected rotatably, but axially secure as regards displacement, with the guide element. Through this configuration, additional parts of the device, arranged in the housing, which are connected with the guide element, are displaced axially when the receptacle holder is mounted on the housing. Thereby, the administering device may be automatically reset for example on detaching of the receptacle holder, and on fastening of the receptacle holder, it can be brought into a state ready for operation again. Upon detaching of the receptacle holder, the interior of the device (e.g., the drive arrangement and, if applicable, a triggering arrangement connected therewith) may be moved in a distal direction so that the triggering arrangement, which can be formed as a push button, is drawn into the housing and thus indicates that the device is not ready for operation.

In some embodiments, the carrier element may be guided with respect to the housing such that on fastening of the receptacle holder to the housing, it is entrained by the receptacle holder and is set into a combined rotational movement relative the housing about the rotation axis and translation movement along the rotation axis in a proximal direction.

In some embodiments, the carrier element may be moveable between two defined final positions, and the detent element brings about in both positions a detachable detent connection, by which the carrier element is fixed relative to the housing. The carrier element assumes its first final position when the receptacle holder assumes its holding position, and assumes its second final position when the receptacle holder is removed from the housing. The detent element may be detachably engaged both in the first final position and also in the second final position directly with the carrier element.

In some embodiments, the carrier element may be guided in at least one guide slit relative to the housing, i.e., on the housing itself or on an element which is fixed to the housing by one or more corresponding pins. Upon fastening to the housing, the receptacle holder may be guided in at least one guide slit, in the manner of a bayonet connection, relative to the housing.

In some embodiments, the detent element may be constructed in the form of a ring which extends around the rotation axis and/or around the thrust element. Suitable detent noses can be constructed on the ring. The detent element may be axially spring-loaded by a separate spring element. This may be, for example, a helical spring subjected to pressure, or another type of elastic element. However, the spring element may be configured as a ring extending around the rotation axis and may be curved about an axis perpendicularly to the rotation axis, so that the spring force is produced by a compressing of the spring element along the rotation axis.

In some embodiments, the detent element may be constructed integrally with the spring element, and the detent element can be constructed as a projection, protruding in the direction of the rotation axis, on the spring element. The detent element may be provided in this manner when the spring element has a curved ring configuration.

In some embodiments, the device may further comprise at least one ball bearing, which absorbs forces which are transmitted between the delivery element and the housing. By a ball bearing being provided, frictional losses caused during the administering, due to the transmission of forces between the delivery element and the housing, are largely minimized. A ball bearing may be provided when the device comprises at least one rotatable element cooperating with the delivery element, and a drive arrangement for generating a rotary movement of the rotatable element relative to the housing, with the rotary movement of the rotatable element bringing about a thrust movement, e.g., linear thrust movement, of the delivery element along the thrust axis in a distal direction, by a thread engagement, e.g., a non-locking threaded engagement. In this case, the ball bearing may be arranged such that it absorbs (axial) forces acting along the thrust axis, which are transmitted from the delivery element, and which may be locked with respect to rotation relative to the housing, via the rotatable element to the housing, i.e., which act between the rotatable element and the housing. That is, axial forces acting in a proximal direction may be transmitted between the delivery element and the housing via a rotatable connection, which is secure with respect to displacement in the axial direction. In known devices, a sliding connection is generally provided between the rotatable element and the housing or an element which is fixed to the housing. In some of the exemplary embodiments described herein, on the other hand, at least one ball bearing is provided, which may be arranged between the rotatable element or an element connected therewith on the one hand, and the housing or an element which is fixed to the housing at least during the administering, on the other hand. Thereby, frictional losses during the rotation of the rotatable element can be avoided.

In further embodiments, two ball bearings are provided, and may be arranged so that they can absorb forces along the thrust axis both in a proximal direction and also in the distal direction opposite thereto, i.e., the direction in which the thrust takes place. Axial forces in the proximal direction occur during the administering, whereas axial forces in the distal direction may occur when the delivery element is spring-loaded in the distal direction. The spring serving for this may be arranged and configured with a relatively weak resistance such that it does not cause any ejection of the product out of the reservoir. Rather, it serves, in a change of reservoir, to automatically bring the delivery element into its distal final position, i.e., to move it outward, when the reservoir is removed from the housing. When the delivery element is in a suitable connection with the rotatable element, this leads to the rotatable element being set into a rotation when the delivery element moves out due to the spring force. To keep the spring force low, a ball bearing may facilitate this because with the moving out of the delivery element, the ball bearing minimizes frictional forces.

BRIEF DESCRIPTION OF THE DRAWINGS

FIG. 6 is a perspective view of a coupling sleeve;

FIG. 12A is a perspective view of a coupling shaft with a dose limiting ring of the injection device of FIG. 1A;

FIG. 12B is the parts of FIG. 12A in an exploded view;

FIG. 13 is an exploded view of an arresting sleeve, a coupling spring and a support ring;

DETAILED DESCRIPTION

Figure 1:
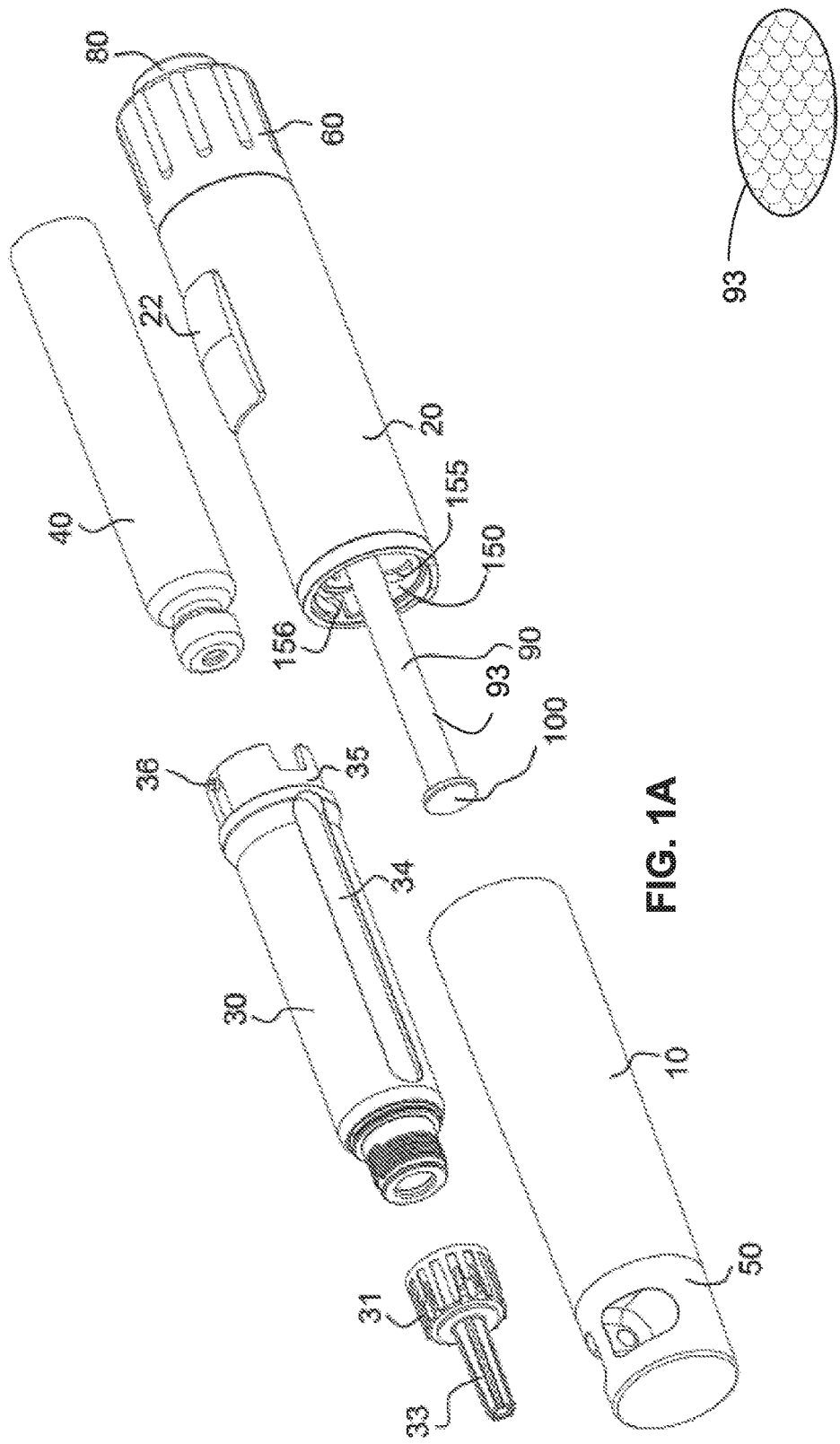
FIG. 1A is a perspective exploded view of an exemplary embodiment of an injection device according to the present invention.
FIG. 1B is a detail view of a surface structure provided on the thrust sleeve.
Figure 2:
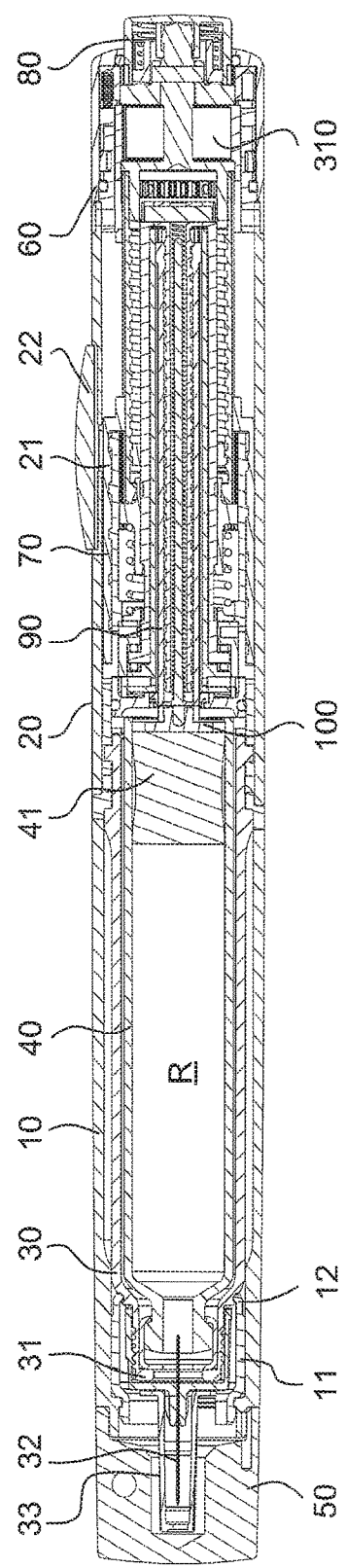
FIG. 2 is a longitudinal section through the injection device of FIG. 1A.

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc. Generally, unless otherwise indicated, relative positional or orientational terms (e.g., upwardly, downwardly, above, below, etc.) are intended to be descriptive, not limiting. FIG. 1A depicts an injection device in the form of an injection pen in a perspective exploded view. FIG. 2 shows the device in longitudinal section. The following description relates to the device in the assembled state, as is illustrated in FIG. 2.

The injection device has a housing sleeve 20 in which a mechanism is housed for setting and distributing a dose. The housing sleeve 20 has substantially the form of a circular cylinder and defines a longitudinal axis. A receptacle holder in the form of a carpule sleeve 30 is detachably fastened to a distal end of the housing sleeve 20 by a bayonet connection, which is described in further detail below. This receives a receptacle in the form of a carpule 40 with a fluid medicament, in which a stopper 41 is displaceably guided. A medicament reservoir R of changeable volume is thereby delimited inside the carpule. Instead of a carpule, a different receptacle can also be present, the volume of which is changeable, e.g., a receptacle with walls folded in a concertina-like manner in the manner of a bellows. The content of the carpule 40 may be monitored through an elongated viewing window 34 in the carpule sleeve 30. A needle holder 31 is screwed on the distal end of the carpule sleeve 30, which needle holder 31 carries a hollow needle (cannula) 32, serving as injection needle, the proximal end of which projects through a sealing septum into the medicament reservoir R. A removable needle protection sleeve 33 surrounds the forwardly projecting region of the needle 32 and protects a user from being pricked accidentally. A protective sleeve 10, the distal end of which is permanently closed by a protective cap 50, is pushed over the carpule sleeve 30. A holding ring 11 with detent arms 12 extending in the proximal direction is mounted inside the protective sleeve 10. The ends of the detent arms 12 are detachably engaged with the carpule sleeve 30. The proposed embodiments are described here by an injection device which has a needle 32, but it is also conceivable that the injection device has several needles or no needle, as in a jet injector.

At the proximal end of the housing sleeve 20, a dosing sleeve 60 is rotatably arranged with a push button 80 held therein. The dosing sleeve serves for the setting of a dose, which is to be distributed from the medicament reservoir R, and for the tensioning of a drive arrangement with a drive element in the form of a spiral spring 310, acting as a torsion spring. The set dose is displayed on a display drum 70, and can be read through a window 21 in the housing sleeve 20, which is covered by a transparent covering 22. A correcting (reduction) of the set dose may be possible by turning back the dosing sleeve 60, which is described in further detail below.

With reference to these parts, the following directions can be defined, which will be referred to consistently below: The distal (forward) direction is the direction in which the administering takes place, i.e., it points along the longitudinal axis from the push button 80 in the direction of the hollow needle 32. The proximal (rearward) direction is accordingly defined as the opposite direction. If reference is made to a direction of rotation (clockwise, anticlockwise), this means the direction of rotation which one observes when one views along the longitudinal axis in the distal direction.

After the setting of the dose, the hollow needle 32 is pierced through the skin of the patient, and a distribution of the dose is triggered by the user pushing the push button 80 into the dosing sleeve 60. A rotary movement is produced by the drive arrangement via a mechanism, which is described in detail below, this rotary movement being converted into an advancing of a delivery element in the form of a thrust sleeve 90 in the distal direction. The thrust sleeve 90 pushes the stopper 41 of the medicament carpule 40 by the set amount in the distal direction via a thrust flange 100 arranged at its distal end, whereby the distribution of the medicament is brought about out of the reservoir R. The thrust sleeve 90 therefore acts as a piston rod for the piston which is formed by the thrust flange 100 and the stopper 41. After the end of the administering, the user releases the push button 80 again. During the advance of the thrust sleeve 90, the display drum is entrained by the drive arrangement such that it returns to its zero position in the course of the distribution. The injection pen is thereby immediately ready for the next dose setting.

When the medicament or therapeutic substance in the medicament reservoir R is running low, i.e. the thrust sleeve 90 is almost completely extended, this is detected by a dose limiting arrangement in the injection pen, which is described in further detail below. The dose limiting arrangement allows the user to set as a maximum the remaining available residual dose. In a subsequent carpule or ampuole change, the dose limiting arrangement and also the display drum 70 automatically return into the initial state, and manual resetting may be unnecessary.

The structure and mode of operation of the mechanism are described in detail below.

Figure 3:
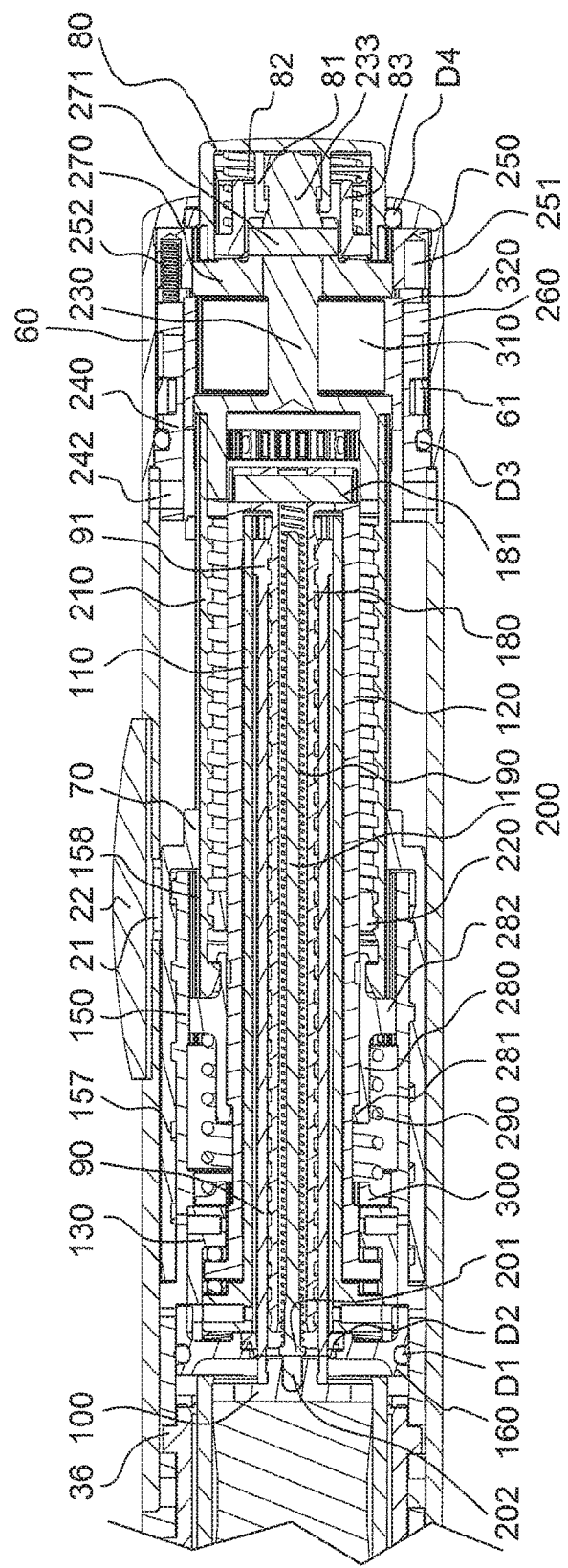
FIG. 3 is an enlarged cut-out of FIG. 2.

FIG. 3 shows an enlarged illustration of the rear (proximal) region of the injection device of FIG. 1A. The structure of this region will now be described in detail substantially from the interior outwardly.

The thrust sleeve 90 is mounted in a guide sleeve 110, arranged such that it is locked against relative rotation with respect to the housing and displaceably, locked against relative rotation and displaceably in the longitudinal direction. For this, the thrust sleeve 90 has, at its proximal end, several radially outwardly projecting guide cams 91, which are guided in longitudinal grooves, complementary thereto, on the inner side of the guide sleeve 110.

Figure 4:
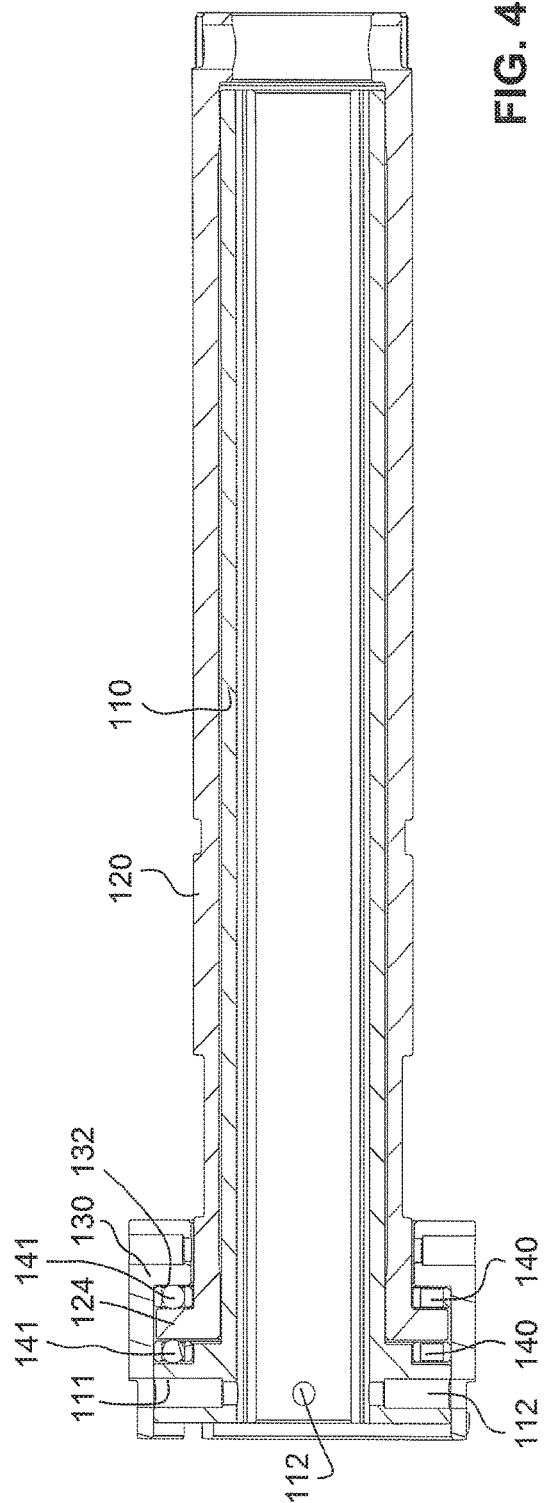
FIG. 4 is a longitudinal section through an arrangement of a guide sleeve and of a coupling sleeve in the injection device of FIG. 1A.

The guide sleeve 110 can be seen in FIG. 4, which illustrates the cooperation of the guide sleeve 110 with further parts. The guide sleeve 110 has at its distal end a radially outwardly projecting, circumferential ring flange 111 with radial bores 112. A ring-shaped bearing holder 130 is pushed from the proximal side via the guide sleeve 110, surrounds the ring flange 111 radially and is connected rigidly therewith via radial cylinder pins, which are not illustrated in the drawings.

A coupling sleeve 120 is rotatably mounted between the ring flange 111 of the guide sleeve 110 and an inwardly projecting shoulder 132 of the bearing holder 130. As is described in further detail below, the coupling sleeve 120 is connected via a threaded rod 180 with the thrust sleeve 90 and therefore forms a part of a delivery arrangement, which is driven by a rotary movement and brings about a thrust of the delivery element in the form of the thrust sleeve. The coupling sleeve 120 therefore absorbs considerable axial forces in operation, which are transmitted via its bearing onto the guide sleeve 110, the bearing holder 130, the mechanism holder 150 and therefore to the housing.

To construct the bearing so as to be low-loss, the bearing includes ball bearings for providing relatively low friction to a rotating unit. Accordingly, a first ball bearing ring 140 is provided between the flange 111 of the guide sleeve and a radially encircling flange 124 of the coupling sleeve 120. A further such ball bearing ring 140 is arranged between the flange 124 and an end face of the bearing holder 130.

Figure 5B:
FIG. 5B is a sectional view of the ball bearing ring in the plane A-A.
Figure 5A:
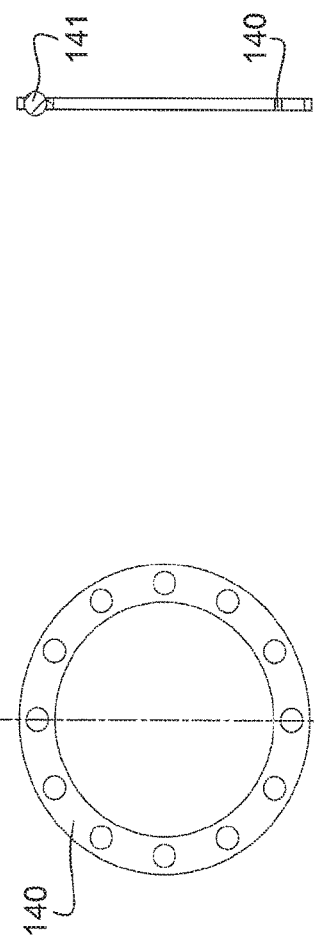
FIG. 5A is a top view onto a ball bearing ring.

The ball bearing ring 140 is illustrated in detail in FIGS. 5A and 5B. It carries a plurality of bearing balls 141, i.e., twelve, but may include a range of bearing balls such as from 3 to 24. The bearing balls 141 run or roll, as can be seen in FIG. 3, in flat, circular grooves formed in both end faces of the radial flange 124 of the coupling sleeve 120, in the corresponding end face of the flange 111 of the guide sleeve 110 and in the end face of the bearing holder 130.

The coupling sleeve 120 is illustrated in FIG. 6, together with the ball bearing rings 140 (but without balls 141). On the cylindrical sleeve body 121, a plurality of longitudinal ribs 122 are formed, which extend over a considerable part of the length of the sleeve body in a longitudinal direction up to its proximal end. Corresponding grooves are provided therebetween. From a thickening area 123, the flange 124 follows towards the front, which adjoins the ball bearing rings 140 on both sides.

Figure 7:
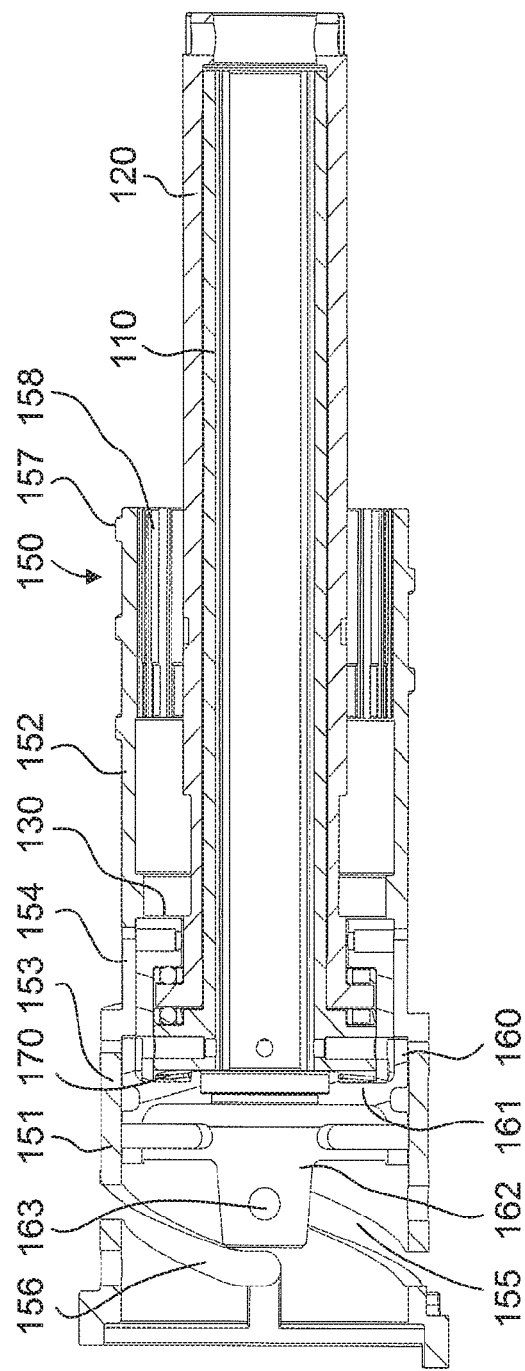
FIG. 7 is a longitudinal section through selected parts of the injection device of FIG. 1A.

FIG. 7 illustrates how the unit of guide sleeve 110 and bearing holder 130 is held in a sleeve-shaped mechanism holder 150, so as to be locked against relative rotation, but displaceably arranged in the longitudinal direction.

The mechanism holder 150 includes a distal section 151 with increased internal and external diameter and a proximal section 152 with a somewhat smaller internal and external diameter. These two sections are connected by a step 153. The outer side of the distal section 151 is held rigidly in the housing sleeve 20. Thereby, the mechanism holder 150 may be immovable with respect to the housing, therefore forming functionally a part of the housing.

Adjoining the step 153, at least two longitudinal slits 154 are formed in the mechanism holder 150. Pins, which are not illustrated in FIG. 7, are inserted in the bearing holder 130. These project radially beyond the bearing holder 130 and into the longitudinal slits 154 of the mechanism holder. The bearing holder 130 and the guide sleeve 110, which is securely connected therewith, may thus be guided displaceably between a distal and a proximal final position and so as to be secured with regard to rotation in the mechanism holder 150. Toward the proximal end, on the outer covering surface of the mechanism holder 150, an external thread 157 is formed. Several longitudinal grooves 158 are formed in this region on the inner surface.

Figure 8:
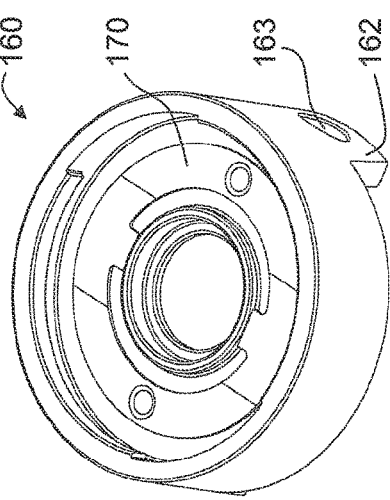
FIG. 8 is a perspective illustration of a bayonet sleeve.

In the distal direction, a bayonet sleeve 160 adjoins the guide sleeve 110 and the bearing holder 130, which is also illustrated in FIG. 8. It is held on the bearing holder 130 in the axial direction and is rotatable with respect thereto. With an inwardly projecting ring flange 161, the bayonet sleeve 160 supports the unit of guide sleeve 110 and bearing holder 130, with coupling sleeve 120 held therein, in the distal direction. The bayonet sleeve 160 has two arms 162 projecting axially in the distal direction and lying diametrically opposite each other, which arms 162 have radial openings 163. Radially outwardly projecting pins are inserted into these openings, which pins run in two guide slits 155 of the mechanism holder 150 acting as connecting link guides (positive guides). Guide slits 155 are configured so that the bayonet sleeve 160, with an anticlockwise rotation (in the sense of the definition indicated above, i.e., on observation along the longitudinal axis in the distal direction) is compulsorily also moved axially in the proximal direction. In this way, the unit of guide sleeve 110, bearing holder 130 and coupling sleeve 120 is moved in the proximal direction. Vice versa, with a rotation of the bayonet sleeve 160 clockwise, this unit moves in the distal direction. Parallel to the guide slits 155, a further pair of guide slits 156 runs, in order to receive radial pins 36 of a locking region 35 of the carpule sleeve 30 (cf. FIGS. 1 and 3). On introduction of the carpule sleeve 30 into the housing, the carpule sleeve is also subject to a positive guidance, so that the carpule sleeve 30 performs a combined rotary movement and displacement. The carpule sleeve 30 is configured such that, upon its movement, it is coupled with the arms 162 of the bayonet sleeve 160 and entrains the bayonet sleeve 160.

The guide slits 155 are of finite length and delimit the movement of the bayonet sleeve between a distal and a proximal final position. In FIG. 7, the proximal final position is illustrated in which the guide slits 155 allow a rotation of the bayonet sleeve through 90 degrees between these positions.

Figure 9A:
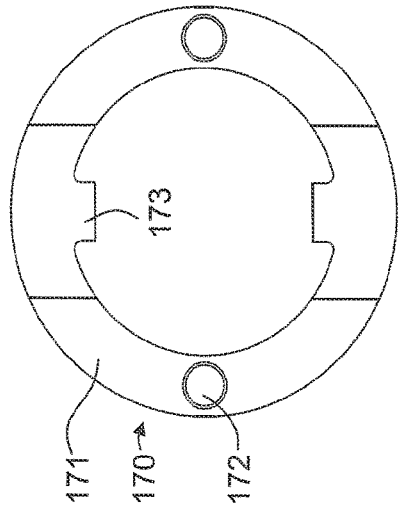
FIG. 9A is a top view onto a bayonet spring.
Figure 9C:
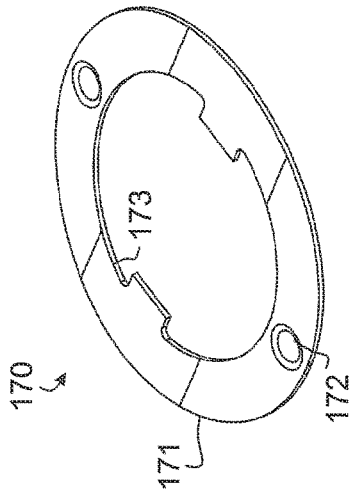
FIG. 9C is a perspective view of the bayonet spring of FIG. 9A.
Figure 9B:
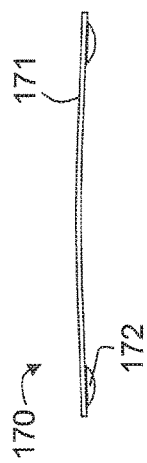
FIG. 9B is a side view of the bayonet spring of FIG. 9A.

To fix the bayonet sleeve detachably in its two final positions so as to be locked against relative rotation with respect to the guide sleeve 110, and thus with respect to the housing sleeve 20, a bayonet spring 170 is arranged between the bayonet sleeve 160 and the guide sleeve 110. This is illustrated, in detail, in FIGS. 9A to 9C. The bayonet spring 170 has a substantially flat and ring-shaped base body 171 acting as a spring element. Two diametrically opposite, axially flatly projecting bulges or projections 172 protrude out from this base body as detent elements or detent cams axially in the distal direction. Two diametrically opposite flat tongues 173 protrude inwardly and come to lie in corresponding flat recesses of the guide sleeve 110. Thereby, the bayonet spring 170 is held, so as to be secured with regard to torsion, on the guide sleeve 110. As can be seen from FIG. 9B, the base body 171 is bent slightly about an axis perpendicular to the longitudinal axis, and namely such that the curvature mid-point lies on the same side of the bayonet spring as the projections 172 (i.e., distal). As a result, the bayonet spring 170 is pre-stressed between the guide sleeve 110 and the bayonet sleeve 160 permanently such that the projections 172 are pressed in the distal direction against the corresponding counter-surface on the ring flange 161. In this counter-surface, four depressions are present, which are arranged at intervals of 90 degrees about the longitudinal axis. In the proximal final position, the projections 172 come to lie in a first pair of these depressions, whereas in the distal final position, in which the bayonet sleeve is turned through 90 degrees, they are held in the second pair of the depressions. Thereby, two defined detent positions are provided, in which the bayonet sleeve 160 engages via the bayonet spring 170 with the projections 172 detachably with the guide sleeve 110. In both positions, a certain force may need to be overcome to move the bayonet sleeve in the direction of the respective other final position again. Each of the depression pairs may comprise a different configuration, e.g., depth and/or shape, so that a different releasing force is necessary in the two detent positions.

In one detent position, the carpule sleeve 30 is held via its coupling with the bayonet sleeve 160 to be secure with regard to rotation and displacement on the guide sleeve 110, and thus on the housing. In the other detent position, the carpule sleeve 30 is detached from the housing. In this position, the bayonet sleeve 160 is again engaged with the guide sleeve 110 and is thereby fixed on the housing 20 so as to be secure with regard to rotation and displacement. In this way, the carpule sleeve, on insertion into the guide slits 156, locates the arms 162 of the bayonet sleeve in the correct position around the longitudinal axis, and can entrain these upon the releasing of the detent connection.

In the present example, the detent elements are constructed as projections 172 integrally formed with the spring element in the form of the base body 171. Alternatively, a separate detent element may be provided, e.g., in the form of a rigid ring with detent cams, which may be pressed in the axial direction by the spring element. As an alternate to projections, the detent element may also have depressions, which then cooperate with corresponding projections of the counter surface. In the present example, the detent element is locked against relative rotation with respect to the housing. Alternatively, it can also be locked against relative rotation with respect to the bayonet sleeve. The spring element may also have an alterative configuration to produce an axial force. Accordingly, various modifications of locking between the carpule sleeve 30 and the housing are contemplated.

Figure 10:
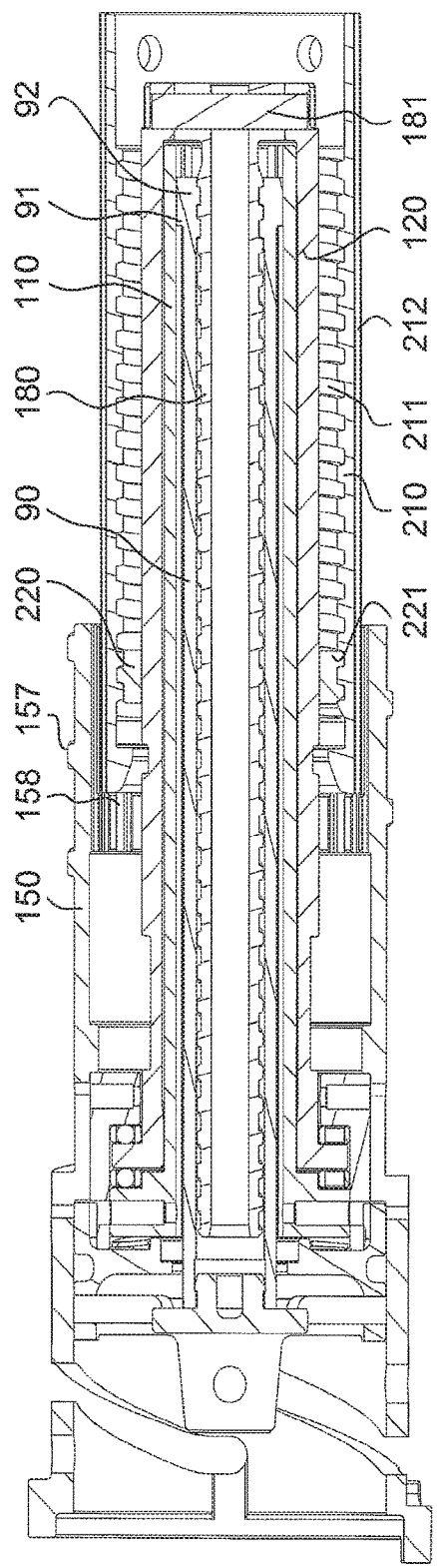
FIG. 10 is a longitudinal section through selected parts of the injection device of FIG. 1A.

In FIG. 10, the parts of the injection device illustrated in FIG. 7 are illustrated together with the thrust sleeve 90 arranged in the guide sleeve 110. At its proximal end, the thrust sleeve 90 has a short internal thread 92 in which a hollow external threaded rod 180 is guided. The latter is connected at its proximal end rigidly with the coupling sleeve 120 via a transverse pin 181. A thrust of the thrust sleeve 90 in the distal direction takes place, by the coupling sleeve 120, which is rotatably mounted, carrying out a rotary movement. As a result of the rigid connection between coupling sleeve 120 and external threaded rod 180, this rotary movement also brings about a rotation of the external threaded rod 180. The thrust sleeve 90 runs with its internal thread 92 on the external threaded rod 180, similar to a nut. The thrust sleeve 90 is locked against relative rotation with respect to the guide sleeve 110, because it runs via the guide cams 91 in longitudinal grooves on the inner side of the guide sleeve 110. In this way, the thrust sleeve 90 is advanced axially on a rotation of the external threaded rod 180. Accordingly, a rotary movement of the coupling sleeve 120 is converted into an axial displacement of the thrust sleeve 90.

As can be seen from FIG. 3, the thrust sleeve 90 is assisted in this thrust movement by a long helical spring 190, which is subjected to pressure, and which is arranged in the interior of the threaded rod 180 and is guided on a guide needle 200. The helical spring 190 presses a ring-shaped thickening 201 close to the distal end of the guide needle 200 in the distal direction against the thrust flange 100. An axial pin 202 projects into a corresponding blind-end bore of the thrust flange 100 and is rotatable in this blind-end bore.

Figure 12C:
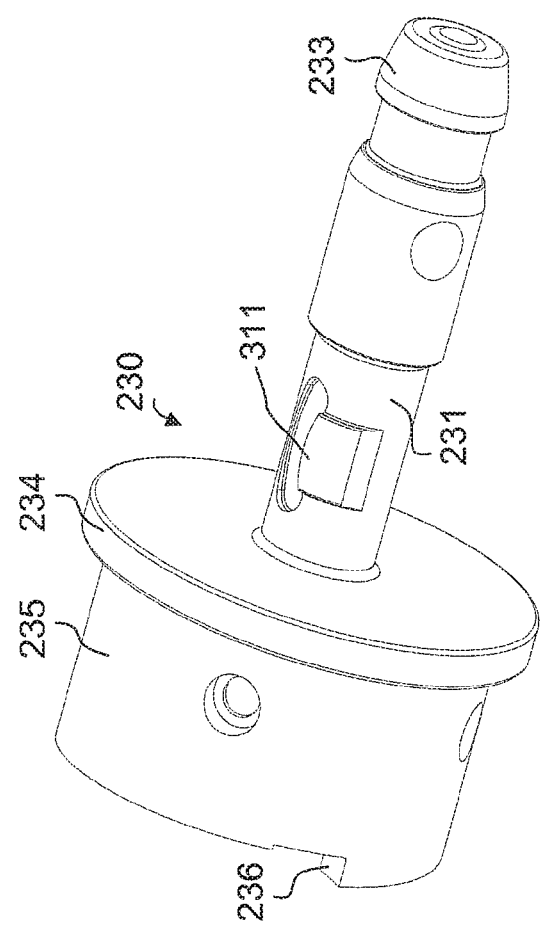
FIG. 12C is the coupling shaft of FIG. 12A in a perspective view from another direction of view.

Furthermore, in FIG. 10 a substantially cylindrical transmission sleeve 210 is inserted into the mechanism holder 150 from the proximal side, which transmission sleeve partially surrounds the coupling sleeve 120. The transmission sleeve 210 has on the outer side a plurality of longitudinal ribs 212. The external diameter of the transmission sleeve 210 is selected here so that, despite its external longitudinal ribs, it is freely rotatable inside the mechanism holder 150. On the inner side, the transmission sleeve 210 has an internal thread 211, in which a dose limiting ring 220 runs with a corresponding external thread 221. In the interior of the dose limiting ring 220, longitudinal grooves 222 are present which can be seen in FIGS. 12A and 12B, into which the longitudinal ribs 122 of the coupling sleeve 120 (cf. FIG. 6) engage. Thereby, the dose limiting ring 220 is movable on the one hand so as to be secure with regard to rotation in the axial direction on the coupling sleeve, and on the other hand is guided in the internal thread of the transmission sleeve 210. A rotation of the coupling sleeve 120 with respect to the transmission sleeve 210 therefore leads to a rotation and axial displacement of the dose limiting ring 220.

The axial displacement range of the dose limiting ring is limited in the distal and proximal directions. This is described in conjuntion with FIGS. 11A, 11B, 12A and 12B.

Figure 11A:
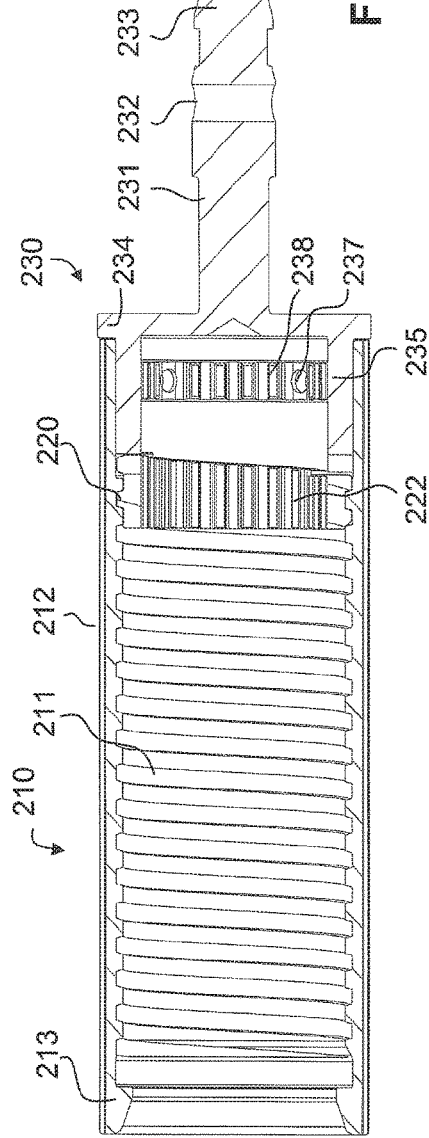
FIG. 11A is a longitudinal section through selected parts of the injection device of FIG. 1A with a dose limiting ring in its final position.
Figure 11B:
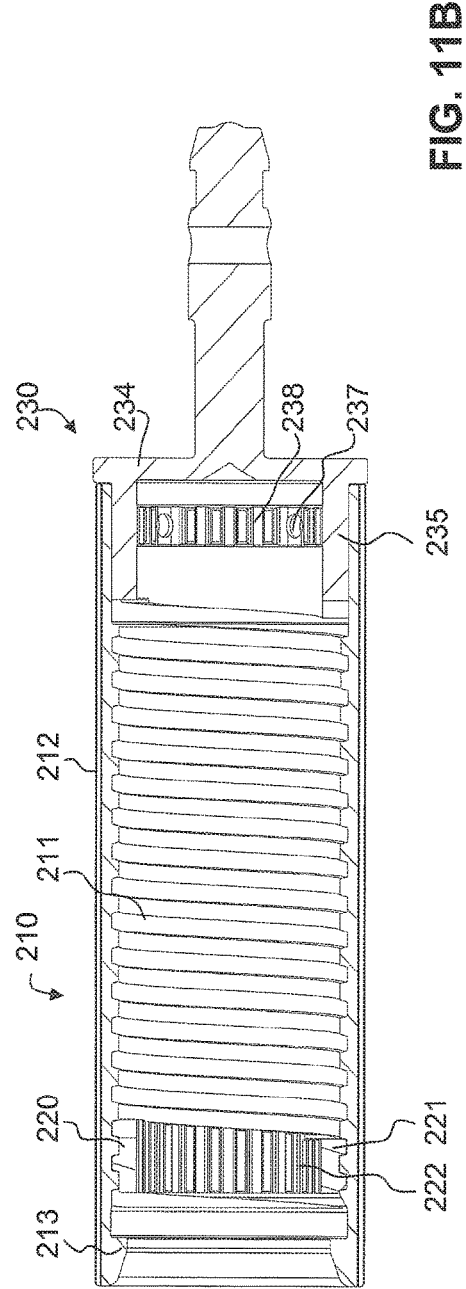
FIG. 11B is a longitudinal section through selected parts of the injection device of FIG. 1A with the dose limiting ring in its initial position.

In FIGS. 11A and 11B, a coupling shaft 230 is connected with the transmission sleeve 210. The coupling shaft comprises an axis 231 with a transverse bore 232 close to the proximal end 233. A circumferential flange 234 extends radially outwardly from the distal end of the axis. A ring flange 235 extends in turn therefrom axially in the distal direction. The external diameter of the circumferential flange 234 is greater than that of the ring flange 235, whereby the circumferential flange 234 protrudes radially over the ring flange 235, and forms a stop for the transmission sleeve 210. The ring flange 235 is pushed into the transmission sleeve 210, so that the latter lies with its proximal end against the circumferential flange 234. The ring flange is secured by radial pins in the transmission sleeve 210, which are pushed into bores 237. Thereby, the coupling shaft 230 and the transmission sleeve 210 are connected with each other so as to be locked against relative rotation and secured against displacement. Several longitudinal grooves 238 are formed in the inner surface of the ring flange 235.

FIGS. 12A and 12B show the coupling shaft 230 and the dose limiting ring 220 alone. A radial stop 223, which cooperates with a corresponding radial stop 236 on the ring flange 235 of the coupling shaft, is formed on the dose limiting ring 220. A radial stop is understood to mean a stop surface, the surface normal of which points substantially in the tangential direction, and which is formed to cooperate with a corresponding counter surface. The radial stop is therefore primarily stressed in a tangential direction (i.e., in a rotational direction) instead of in an axial direction. Thereby, a radial stop avoids the risk of jamming, such as when two parts collide axially via a screw connection, e.g., in the case of a small pitch of the helical thread. The radial stop 236 delimits the screw motion of the dose limiting ring 220 in the proximal direction. In FIG. 11A the dose limiting ring 220 is shown in the resulting proximal final position, and in FIG. 11B on the other hand in a distal initial position.

The proximal end of an arresting sleeve 280 is rotatably clicked into an inwardly directed ring flange 213, chamfered in the distal direction, at the distal end of the transmission sleeve 210. For better clarity, the arresting sleeve 280 is not illustrated in FIG. 10. However, it is shown in FIG. 13. The arresting sleeve comprises a ring-shaped main body 281, from which four arms 282 extend in the distal direction. On its inner surface, the main body has longitudinal grooves 284, which are meshed with the longitudinal ribs 122 of the coupling sleeve 120. Thereby, the arresting sleeve 280 is displaceable in the longitudinal direction relative to the coupling sleeve 120, but is secured as regards torsion with respect thereto. At the end of the arms 282, inwardly extending flange regions 283 are present. The possible displacement range is limited in the proximal direction by these flange regions. These abut in the proximal final position of the arresting sleeve 280, as illustrated in FIG. 3, onto the distal end of the longitudinal ribs 122 of the coupling sleeve 120. Longitudinal ribs are formed on the outer peripheral surface of the main body 281. These longitudinal ribs engage, in the position of FIG. 3, into the inner longitudinal grooves 158 of the mechanism holder 150. Thereby, the arresting sleeve 280 is displaceable in this position axially with respect to the mechanism holder 150, but secured with regard to torsion. The arresting sleeve 280 in this position therefore secures the coupling sleeve 120 against a rotation in the mechanism holder 150. As described further below, the arresting sleeve 280 is, however, displaceable so far in the distal direction that it can come out of engagement with the mechanism holder 150 and is then rotatable with the coupling sleeve 120.

The arresting sleeve 280 is pre-stressed in the proximal direction by a coupling spring 290. The coupling spring is configured as a helical spring, which is subjected to pressure, surrounds the arms 282 of the arresting sleeve 280 and lies with its proximal end against the distal end face of the main body 281. At the distal end of the coupling spring 290, the latter is held on a support ring 300, which abuts against the bearing holder 130 in the distal direction and on the inner side of which longitudinal grooves are formed.

Figure 14:
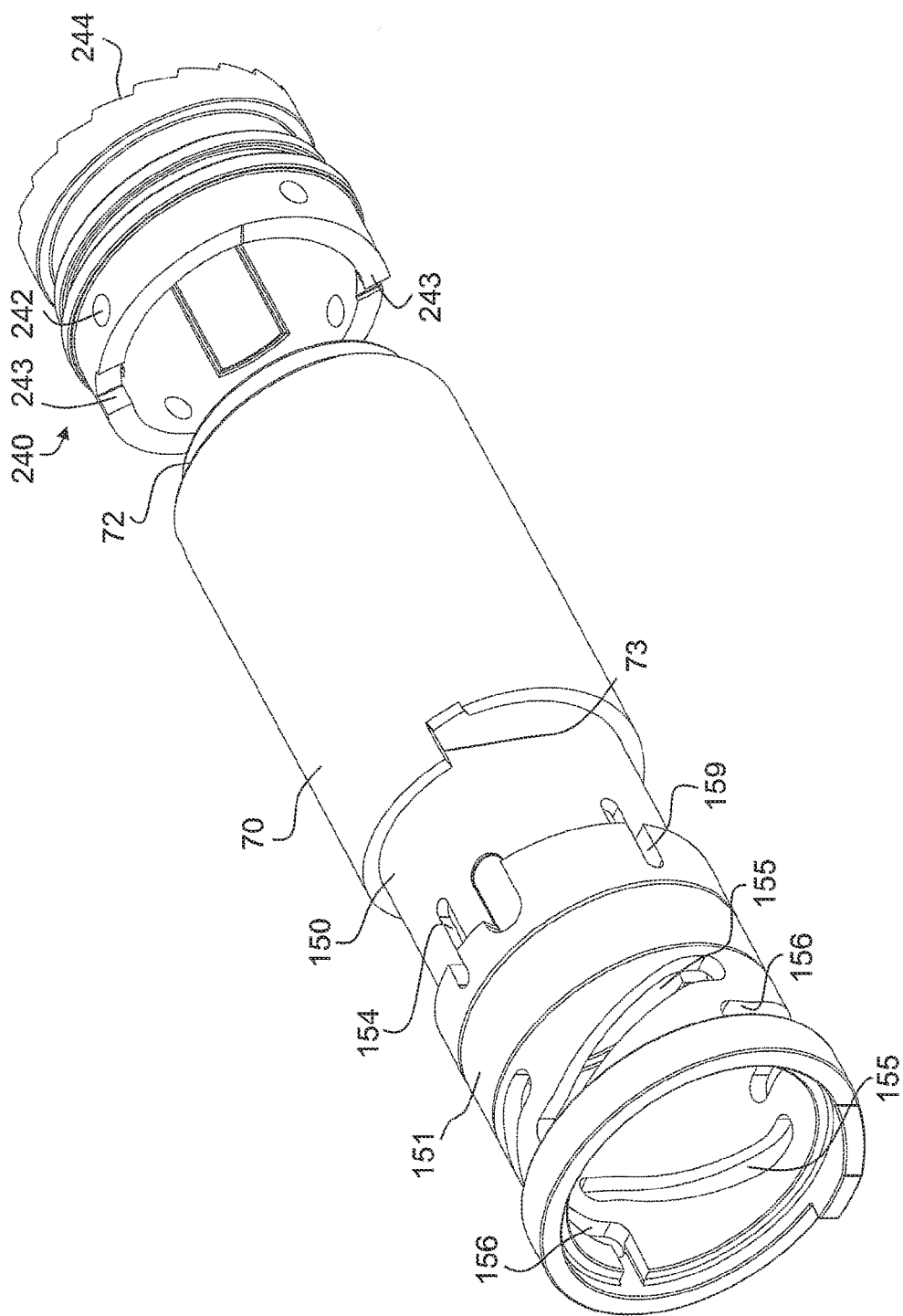
FIG. 14 is a perspective view of selected parts of the injection device of FIG. 1A.

In FIG. 14, the unit of FIG. 10 is illustrated with further components. The display drum 70 is held on the mechanism holder 150. In addition, a stop sleeve 240 is connected immovably with the housing sleeve 20 by pins projecting into the radial holes 242, e.g., see FIG. 14. At the distal end of stop sleeve 240, radial stops 243 are provided, and at the proximal end, teeth 244, e.g., serrated teeth, are arranged on the end face for a ratchet connection, described below.

The display drum 70 has an internal thread, which can be seen in FIG. 3, and runs on the external thread 157 of the mechanism holder, which can be seen in FIGS. 7 and 10. At its proximal end, the display drum 70 narrows to a ring-shaped region 72. Longitudinal grooves are formed on the inner side of the ring-shaped region 72. By these longitudinal grooves, the display drum 70 is secured with regard to torsion, but is guided displaceably in the longitudinal direction on the longitudinal ribs 212 of the transmission sleeve 210. Through the combination of this longitudinal guide on the transmission sleeve and the thread guide on the mechanism holder, a rotation of the transmission sleeve 210 leads to a combined rotation and longitudinal displacement of the display drum 70. This movement is delimited or stopped by radial stops in both directions. At the proximal end, a radial stop cooperates with the radial stop 243 of the stop sleeve 240. At the distal end, a corresponding radial stop 73 cooperates with a radial stop 159 of the mechanism holder 150. Thereby, the screw motion of the display drum 70 is limited in both directions by radial stops.

Figure 15:
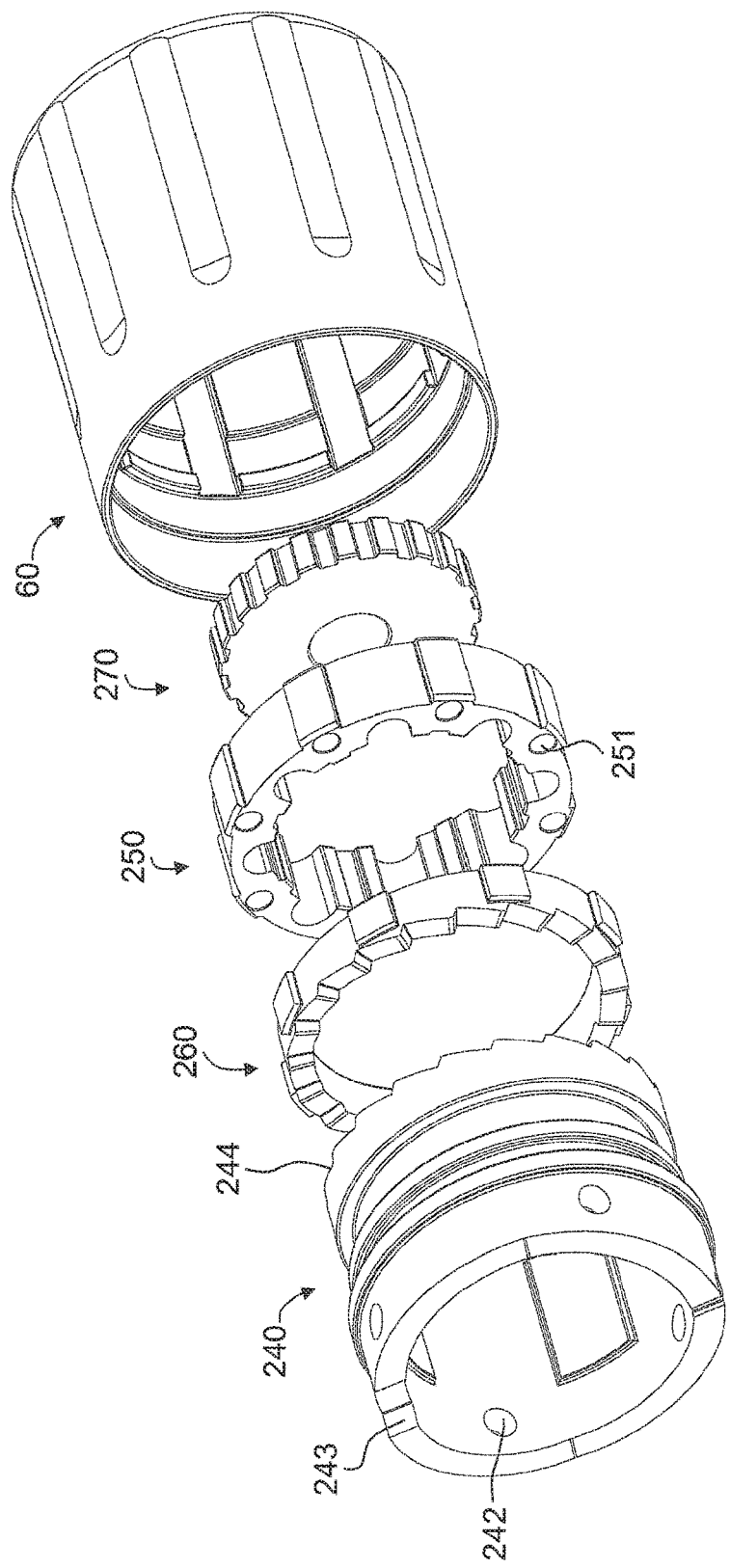
FIG. 15 is a perspective exploded view of the proximal end of the injection device of FIG. 1A.

The mechanism for setting a dose and for triggering its administering is described with reference to FIGS. 3 and 15. The dosing sleeve 60 is arranged at the proximal end of the housing sleeve 20. Dosing sleeve 60 is secured with regard to displacement axially with a spring ring 61 and is fixed rotatably on the stop sleeve 240. The dosing sleeve 60 is rotatable via a slip coupling in the form of a ratchet connection both clockwise and also anticlockwise about the longitudinal axis towards the housing sleeve 20, and is thus configured and arranged to assume several predefined detent positions.

The dose setting mechanism comprises an inner ring 250 arranged inside the dosing sleeve 60 and rigidly connected with the dosing sleeve 60. The inner ring 250 has in its radial inner surface a plurality of longitudinal grooves. In the distal direction from the inner ring 250, a ratchet ring 260 is held axially displaceably but secured with regard to rotation in the dosing sleeve 60. The ratchet ring 260 is serrated on its distal end face, and namely in a complementary manner to the teeth 244 of the serrated proximal end face of the stop sleeve 240, so that teeth of the ratchet ring 260 can engage in depressions on the end face of the stop sleeve 240 and vice versa. The ratchet ring 260 is axially displaceable by a certain amount between the distal end face of the inner ring 250 and the serrated proximal end face of the stop sleeve 240. The amount by which an axial displacement is such that the serrated end faces of the ratchet ring 260 and of the stop sleeve 240 can come out of engagement. The ratchet ring 260 is pressed elastically by an elastic force against the stop sleeve 240. For this, several axial bores 251 are present in the form of blind-end bores in the inner ring 250. Helical springs 252, which are subjected to pressure are inserted in at least one of these bores, e.g., in at least two bores, at a uniform spacing along the circumference of the ring when multiple bores are provided. The helical springs 252 press the ratchet ring elastically against the stop sleeve.

In the position of rest, the ratchet ring 260, with its serrated end face, is in engagement with the serrated end face of the stop sleeve 240. Thereby, the ratchet ring and the dosing sleeve 60 connected therewith assume one of several defined angle positions about the longitudinal axis. With a rotation of the dosing sleeve 60 relative to the housing sleeve 20, the teeth of the ratchet ring 260 and of the stop sleeve 240 slide on each other against the axial spring force of the helical springs 252, until they come out of engagement and arrive in engagement again in the next defined angle position. In this way, an elastically detachable detent connection is produced by rotation with a sufficient torque in several predefined angle positions of the dosing sleeve 60 relative to the housing sleeve 20. This mechanism can also be designated as a double slip coupling.

By rotation of the dosing sleeve 60 clockwise, the spiral spring 310 can be tensioned, which is indicated in FIG. 3. The spiral spring 310 has a plurality of spring coils, which run around the longitudinal axis and are arranged over one another radially to the longitudinal axis. The inner end of the spiral spring 310 is fastened to a spring holding region 311 of the coupling shaft 230, which region can be seen in FIG. 12C. The outer end of the spiral spring 310 is mounted on a spring sleeve 320, which is held so as to be locked against relative rotation in the stop sleeve 240.

A coupling disc 270 is mounted on the coupling shaft 230, and is secured against rotation and displacement by a pin 271 in the transverse bore 232 of the coupling shaft 230. The coupling disc 270 has a plurality of longitudinal ribs on its outer peripheral surface. In the position of FIG. 3, these longitudinal ribs engage into the longitudinal grooves, which are complementary, on the inner side of the inner ring 250, but can be brought out of engagement by an axial displacement.

The dosing sleeve 60 has an axial passage opening, in which the push button 80 is arranged so as to be axially displaceable. The push button 80 is rotatable with a plurality of radially elastic arms 81 and is clicked on the proximal end 233 of the coupling shaft 230 so as to be secured against displacement. It abuts with its distal end against a proximal end face of the coupling disc 270. In the interior of the push button 80 there is a helical spring 82, which lies with its proximal end against the inner end face of the push button and presses with its distal end against a bearing ring 83. The bearing ring 83 has on its outer peripheral face longitudinal ribs, which are guided in corresponding longitudinal grooves in the inner covering surface of the push button 80. Thereby, the support ring 83 is arranged in the push button 80 so as to be locked against relative rotation and so as to be axially displaceable. The bearing ring 83 is configured be serrated in a flat manner on its distal end face. The proximal end face of the coupling disc 270 is formed so as to be serrated in a complementary manner hereto, so that the bearing ring 83 is axially meshed with the coupling disc 270. On distribution of the medicament, the coupling disc 270 rotates with respect to the bearing ring 83. Thereby, the serrated surfaces slide on one another, so that the toothing comes alternately into and out of engagement. Thereby, a characteristic clicking sound is produced, which indicates to the user that an administering is just taking place. The toothing of bearing ring 83 and coupling disc 270 may be configured so that each clicking corresponds to one unit, or of a predetermined multiple of one unit, of the administered medicament.

The mechanism for setting the dose and the distribution may be arranged and configured in the housing sleeve 20 so as to be protected against splashing, i.e., sealed. According to certain embodiments, four seals D1, D2, D3 and D4 may be provided. The seal D1 comprises a sealing ring, which lies in a sealing manner between the mechanism holder 150 and the bayonet sleeve 160. The mechanism holder 150 is mounted immovably and tightly in the housing 2, and the bayonet sleeve 160 is both displaceable and rotatable with respect to the mechanism holder 160 and is sealed with respect to the housing by the seal D1.

The seal D2 comprises a further sealing ring, constructed so as to be flat, which lies in a sealing manner between the bayonet sleeve 160 and the smooth outer side of the thrust sleeve 90. Thrust sleeve 90 may have a smooth (e.g., within accepted and/or manufacturing tolerances) or substantially smooth outer wall region, the length of which corresponds at least to the distance between the distal final position and the proximal initial position of its longitudinal movement, between which the thrust sleeve 90 is movable in the course of the administering. The sealing effect between seal D2 and thrust sleeve 90 may be facilitated by providing an outer wall region of the thrust sleeve 90 with fine structures, e.g. scales, a pattern or texture, in the range below 100 micrometres, e.g. below 10 micrometres, and may be configured as micro- or nano-structuring, at least along the length between the distal final position and the proximal initial position. A thrust sleeve 90 with such micro- or nano-structuring may be considered substantially smooth to one of skill in the art due to the minute size of the structures. However, one of skill in the relevant art would also appreciate the usefulness of such structures in maintaining and/or enhancing a seal between the thrust sleeve 90 and seal D2. In some embodiments, the outer wall region may extend from thrust flange 100 to guide cams 91. In addition, texture or structure provided on the substantially smooth surface may extend along the entire outer wall region or along portions therof. Texture 93 along the thrust sleeve is depicted in FIG. 1B, which is configured as micro-structured scales. In addition or alternatively, other structures, such as surface protrusions or indentations, which may have a desired texture or structure, may be provided along the outer wall region. Such additional or alternative structures may have an orientation such that the structures are directed towards the proximal or distal direction. Furthermore, the thrust flange 100 is arranged tightly on the thrust sleeve 90. The region of the injection device, including the interior of the thrust sleeve 90, lying proximally from the bayonet sleeve 160, may thus be sealed against the region lying distally. Where fluids are introduced into this distal region, e.g., due to a breakage of the medicament carpule 40, the fluid may be prevented from penetrating into the mechanics, thus preventing contamination or jamming.

The other two seals are situated at the proximal end of the injection device. The seal D3 comprises a sealing ring, which lies in a sealing manner between the dosing sleeve 60 and the stop sleeve 240. The stop sleeve 240 is mounted immovably and tightly in the housing sleeve 20, whereas the dosing sleeve 60 is rotatable with respect to the stop sleeve 240. The seal D4 comprises a further sealing ring, which lies in a sealing manner between the dosing sleeve 60 and the push button 80. In addition, a transparent window covering 22 is placed in a fluid-tight manner on the window 21. Accordingly, mechanisms, operational components or mechanics, which are delimited toward the exterior by the housing sleeve 20, the dosing sleeve 60 and the push button 80, are also sealed toward the exterior and may be protected against the penetration of fluids. Rainfall or a glass of water accidentally spilt by the user can therefore also not harm the injection device.

The seal towards the thrust sleeve may be configured such that it acts as a stripper, similar to a windshield wiper in a car. For this, at least towards the distal side, there is as small a contact angle between the surfaces of the sealing element and the thrust sleeve, which may lie below 90 degrees.

Instead of conventional seals or in addition hereto, the parts which are to be sealed with respect to each other may be configured with a hydrophobic surface, such as being formed of or coated with a hydrophobic material. A hydrophobic surface may prevent the parts from being wetted. Drops of water thereby roll off and a leaking of fluids through gaps is efficiently prevented between the parts, which are to be sealed due to capillary effects. The parts provided with a hydrophobic surface, which are to be sealed with respect to each other, may therefore be arranged at a certain distance (gap) from each other, without the sealing effect being lost ("virtual seal").

A hydrophobic surface is understood here to mean a surface for which the contact angle of a water drop is at least 90 degrees, e.g., at least 110 degrees. The contact angle is the angle between the surface normal of the water drop and the respective surface at the contact site. Examples of materials with hydrophobic characteristics are PTFE (polytetrafluoroethylene) or PVDF (polyvinylidene fluoride), as well as other hydrophobic materials that may be formed as thin coatings, e.g., in the range of a few micrometres, to provide a hydrophobic surface.

In experiments, various pens and a sleeve were provided nanotechnologically with a hydrophobic coating. 20 pens with external diameters of 10.0 to 11.9 mm in graduations of 0.1 mm were examined. The pens were arranged centrally in a sleeve with 12 mm internal diameter, which corresponds to gap thicknesses of 0.05 mm to 1.0 mm in graduations of 0.05 mm. The interior of the sleeve was then acted upon with water. A sealing effect up to a gap thickness of approximately 0.5 mm was observed. With reciprocal rotation between pen and sleeve, a sealing effect up to a gap thickness of approximately 0.25 mm was observed.

To improve the sealing effect, the surfaces may be micro- or nano-structured, i.e., provided with structures, the dimensions of which are in the nanometre to micrometre range. These structures can have a selected direction, to inhibit the flow of fluids on the surface in one direction. Thus, for example, scales can be provided.

Figure 16:
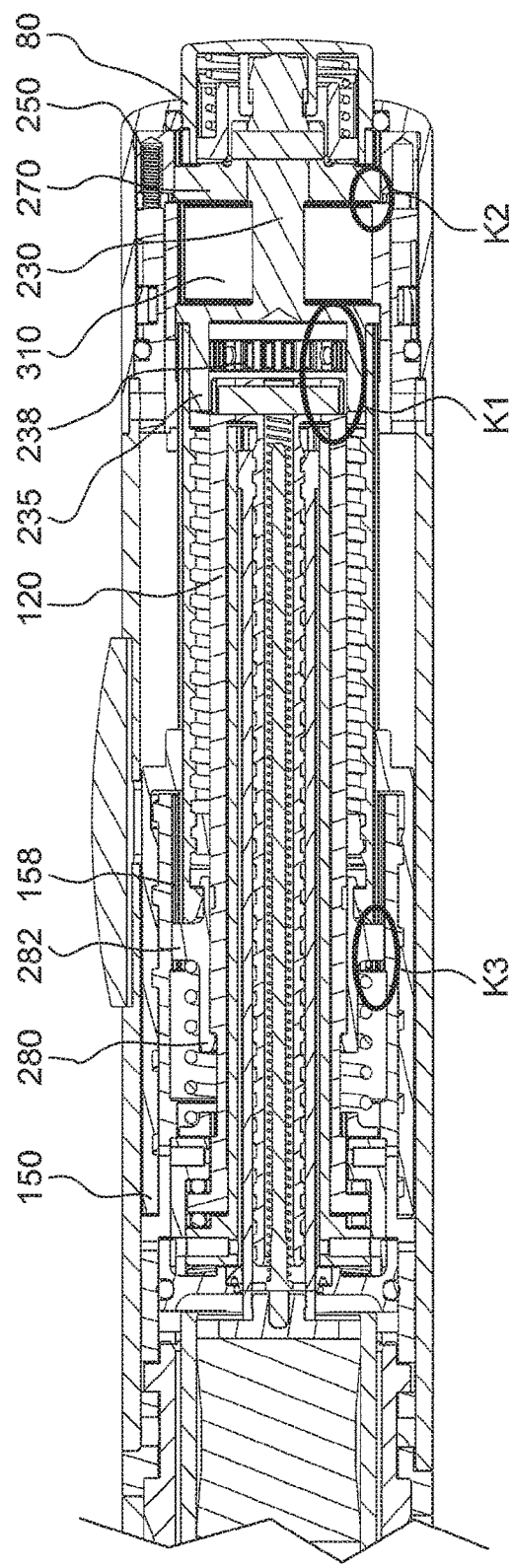
FIG. 16 is a longitudinal section through the injection device of FIG. 1A in the initial position.

The mode of operation of the injection device is now to be described below with reference to FIG. 16, in which an exemplary injection device is illustrated in its initial position before the first use. The mechanism described above for setting and distributing a dose has three couplings K1, K2 and K3 for the transmission of torques. Each of these couplings may be brought into and out of engagement by an axial movement of two components with respect to each other.

The coupling K1 is formed by the longitudinal grooves on the inner surface of the axial flange 235 of the coupling shaft 230 as a coupling input member in cooperation with the longitudinal ribs 122 on the outer side of the coupling sleeve 120 (cf. FIG. 5) as coupling output member. In the position of FIG. 16, this coupling is uncoupled, i.e., the coupling formed by the cooperation of the longitudinal grooves and longitudinal ribs is out of engagement. The coupling K1 can be coupled by an axial displacement of the coupling shaft 230 in the distal direction.

The coupling K2 is formed by the longitudinal grooves in the radial inner surface of the inner ring 250 as a coupling input member in cooperation with the longitudinal ribs on the radial outer surface of the coupling disc 270 as coupling output member. In the position of FIG. 16, this coupling is coupled, i.e., the toothing formed by the longitudinal grooves and longitudinal ribs is in engagement. The coupling K2 can be uncoupled by an axial displacement of the coupling disc 270 in the distal direction.

The coupling K3 is formed by the longitudinal ribs on the outer side of the outer ring flange arms 282 of the arresting sleeve 280 as coupling input member in cooperation with the longitudinal grooves 158 on the inner surface of the mechanism holder 150 as coupling output member. In the position of FIG. 13, this coupling is coupled. It can be uncoupled by an axial displacement of the arresting sleeve 280 in the distal direction.

All three couplings K1, K2 and K3 can be coupled and respectively uncoupled by the push button 80 being displaced axially. On pressing in of the push button 80, the coupling disc 270 and the coupling shaft 230, which is securely connected therewith, are displaced in the distal direction. In this instance, the coupling K1 comes into engagement, i.e., the coupling shaft is coupled for torque transmission with the coupling sleeve 120. At the same time, the coupling shaft 230 advances the transmission sleeve 210 in the distal direction. This entrains the arresting sleeve 280 in the distal direction, whereby the coupling spring 290 is compressed. When the coupling K1 arrives in engagement for the first time, the arresting sleeve 280 is not yet advanced sufficiently far to arrive with its outer ring flange arms 282 out of engagement with the mechanism holder 250. The coupling K3 is therefore initially still coupled. The same applies to the coupling K2: The coupling disc 270 is still in engagement with the inner ring 250. Therefore, all three couplings are coupled. When the push button 80 is pushed in further, the coupling K2 comes out of engagement. With a still further pushing in, coupling K3 comes out of engagement. Therefore, the couplings are as follows: Initial state: K1 uncoupled, K2 and K3 coupled. Pushing in of the push button 80: K1 couples, thereafter K2 uncouples, thereafter K3 uncouples.

Figure 19:
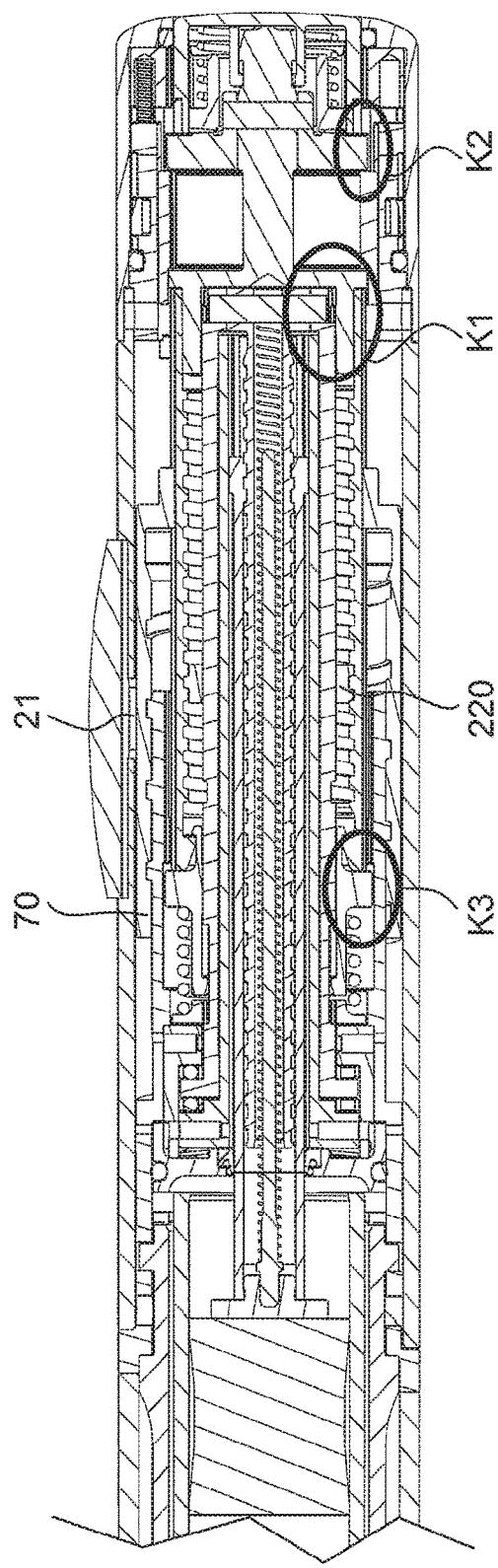
FIG. 19 is the longitudinal section of FIG. 16 after a first triggering and a second increase of dose.

FIG. 19, described further below, shows the injection device with the push button 80 pushed in completely. The coupling K1 is coupled, whereas the couplings K2 and K3 are uncoupled.

On releasing of the push button 80, the engaging of the couplings into each other runs in the reverse sequence. Here, the coupling spring 290 presses the arresting sleeve 280, the transmission sleeve 210, the coupling shaft 230, the coupling disc 270 and the push button 80 back into the distal initial position.

The couplings K1, K2 and K3 and the ratchet connection make possible the systematic transmission of torques between five functionally independent units. A first unit comprises the housing sleeve 20, the mechanism holder 150, the stop sleeve 240 and the spring ring 320. This unit can be regarded functionally as a holding arrangement or as a housing in an extended sense. It constitutes the stationary reference system for all movements.

A second unit comprises the dosing sleeve 60, the inner ring 250 and the ratchet ring 260. It can be regarded functionally as a rotatable dosing arrangement. This dosing arrangement is held detachably on the housing by the ratchet connection, but so as to be secure with regard to torque up to a certain value.

A third unit comprises the coupling disc 270, the coupling shaft 230 and the transmission sleeve 210, which are rigidly connected with each other, and by the spiral spring 310, connected therewith, which acts as the actual drive element. This unit can be regarded as a drive arrangement. The rotary movement of the drive arrangement is limited by two limiting elements, which are both guided on the transmission arrangement. The first limiting element is formed by the display drum 70, which limits the range of movement of the drive arrangement in both directions, a dosing direction and a correction and distribution direction. The second limiting element is formed by the dose limiting ring 220, which limits the range of movement of the drive arrangement at least in one direction, the dosing direction, independently of the first limiting element. The drive arrangement is able to be coupled detachably by the coupling K2 so as to be locked against relative rotation with respect to the dosing arrangement, which makes it possible to tension the drive element in the form of the spiral spring 310.

A fourth unit comprises the coupling sleeve 120 and the threaded rod 180, which form a rigid unit, the elements on which these parts are mounted, namely the guide sleeve 110, the bearing holder 130 and the ball bearing rings 140, and also the thrust sleeve 90. This unit constitutes a delivery arrangement, which converts a rotary movement of an input member in the form of the coupling sleeve 120 into a thrust of the delivery element in the form of the thrust sleeve 90. Its input member is able to be detachably coupled by the coupling K1 so as to be locked against relative rotation with the drive arrangement. In addition, it is able to be detachably coupled via the coupling K3 so as to be locked against relative rotation with the holding arrangement (i.e., the housing).

Furthermore, a triggering arrangement is present, which comprises the push button 80 and serves for the operation of the couplings K1 to K3.

The injection device is operated as follows. Starting from the initial position of FIG. 16, a dose is set, which is to be administered. For this, the dosing sleeve 60 is turned clockwise. In so doing, the dosing sleeve entrains the coupling disc 270 and the coupling shaft 230 via the coupling K2, and the spiral spring 310 is wound up. The torque generated is held by the ratchet connection between the co-rotating ratchet ring 260 and the stationary stop sleeve 240. Through the rotation of the coupling shaft 230, the transmission sleeve 210 and the display drum 70, which is guided thereon, are also co-rotated. The display drum 70, threadably guided on the mechanism holder 150, is additionally displaced axially in the proximal direction, and therefore performs as a whole a screw motion in the proximal direction. Markings on the surface of the display drum 70 pass through under the window 21 and indicate the set dose. Furthermore, the dose limiting ring 220, threadably engaged with the interior of the transmission sleeve 210 and arranged, secured with regard to rotation, on the coupling sleeve 120, is displaced in the proximal direction.

Figure 17:
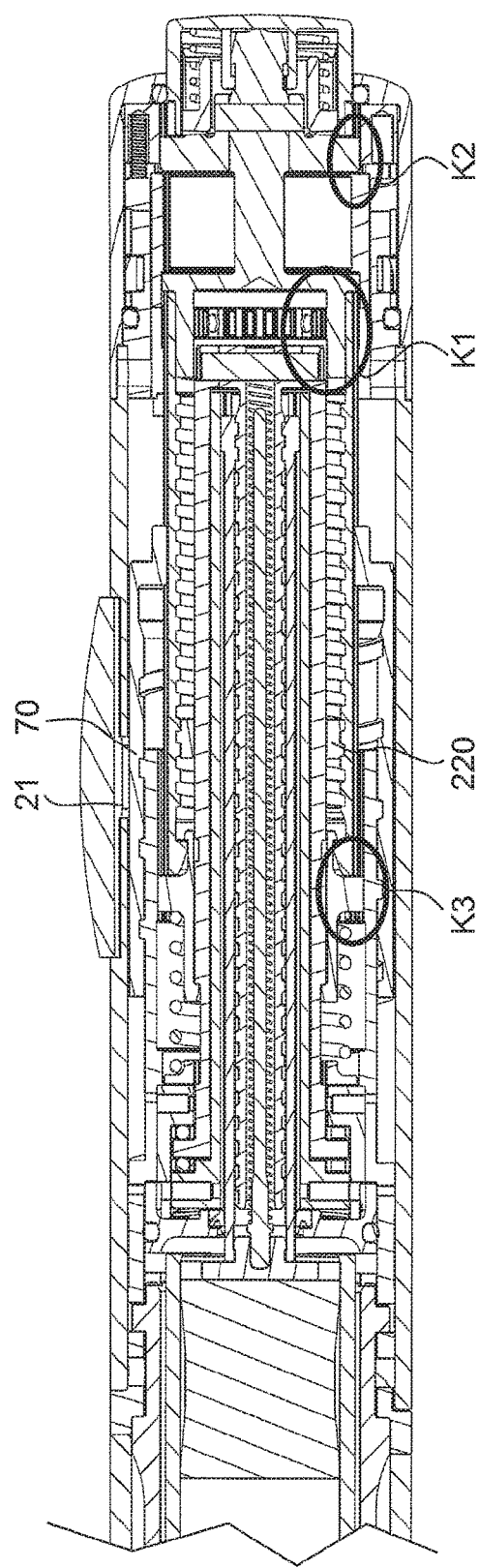
FIG. 17 is the longitudinal section of FIG. 16 after a first increase of dose up to half the maximum dose.

FIG. 17 shows the injection device after half the maximum individual dose has been set. The display drum has travelled rearwardly half-way between its distal (forward) and its proximal (rear) final position. In addition, the dose limiting ring 220 has travelled in the proximal direction by an amount proportional to the individual dose that has been set.

Figure 18:
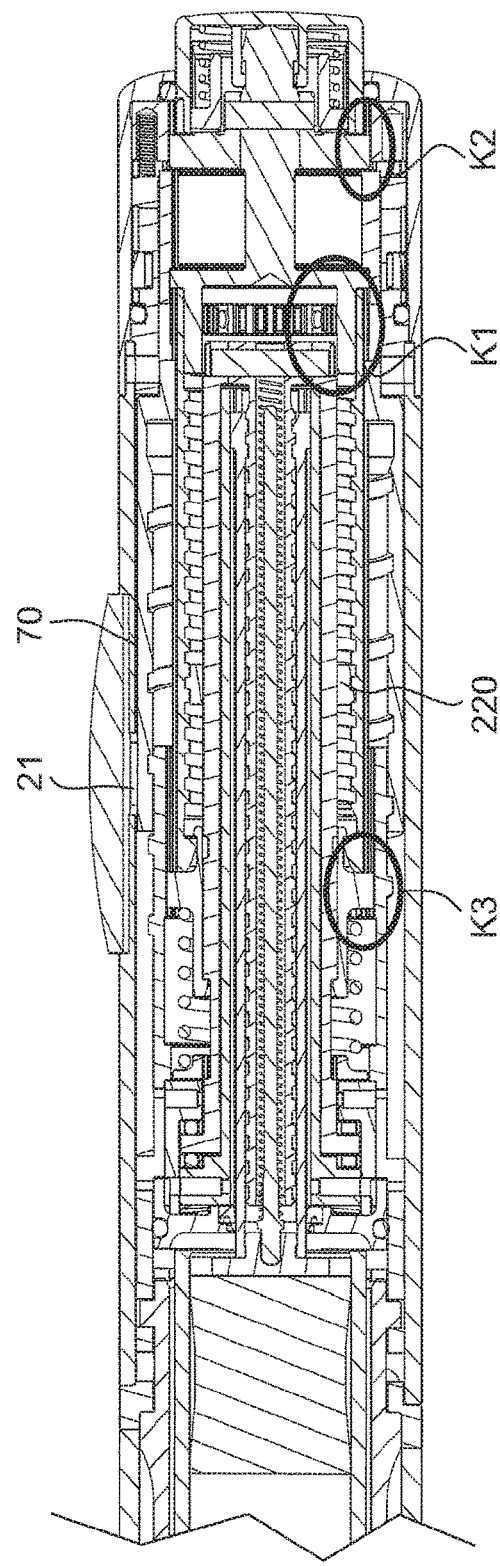
FIG. 18 is the longitudinal section of FIG. 16 after a first increase of dose up to the full maximum dose.

The rotation of the dosing sleeve 60 clockwise is limited, on the one hand, by the maximum movement range of the display drum 70, and on the other hand, by the maximum movement range of the dose limiting ring 220. After a predetermined number of revolutions of the dosing sleeve 60, the display drum 70 abuts with its proximal radial stop against the stop sleeve 240, in so far as the rotation of the dosing sleeve 60 has not been previously limited by the dose limiting ring 220, as is described further below. Thereby, no further rotation of the dosing sleeve 60 is possible. This position corresponds to the maximum individual dose, which can be set. This situation is illustrated in FIG. 18.

If the set dose is to be corrected, i.e., reduced, then the dosing sleeve 60 can be turned back anticlockwise against the force of the ratchet connection. As the ratchet connection in this direction absorbs the torque of the spiral spring 310, the ratchet connection is configured asymmetrically: The toothing on the end face has a larger angle of inclination on the side which is stressed by a torque which acts anticlockwise onto the dosing sleeve than on the side which is stressed with a torque clockwise (cf. the configuration of the teeth 244 in FIG. 14). The angle of inclination is understood here to mean the absolute amount of the angle between the respective flank of a tooth on the end face of the ratchet ring 260 or on the end face of the stop sleeve 240 and a cross-sectional area through the injector.

The distribution or delivery of the dose, which has been set is actuated or initated by the push button 80 being pushed in. In this instance, the coupling K1 is coupled, and a connection is produced which is locked against relative rotation between the coupling shaft 230, on the one hand, and the coupling sleeve 120 and also the threaded rod 180 rigidly connected therewith, on the other hand. All three couplings K1, K2 and K3 are coupled. On further pushing in of the push button 80, the coupling K2 uncouples. Thereby, the connection, which is locked against relative rotation between the dosing sleeve 60, on the one hand, and the coupling shaft 230 with the coupled coupling sleeve 120 and threaded rod 180, on the other hand, is cancelled. This leads to the ratchet connection no longer absorbing the torque of the spiral spring 310. However, the system is held so as to be locked against relative rotation via the coupling K2 in the mechanism holder 150 and hence in the housing sleeve 20. When the push button 80 is pressed further, the coupling K3 also uncouples. At this moment, the torque of the spiral spring 310 becomes free and acts via the coupling shaft 230 and the coupling sleeve 120 on the threaded rod 190.

Hereby, these parts are set in an anticlockwise rotation. Through its thread engagement with the threaded rod 190, the thrust sleeve 90 undergoes an axial displacement in the distal direction. Via the thrust flange 100, the thrust sleeve advances the stopper 41 in the carpule 40. In this way, the medicament is distributed or injected.

During the distribution or injection process, axial forces act on the thrust sleeve 90: The torque of the spiral spring 310 is converted into a force in the thrust direction, which advances the stopper 41 in the carpule 40. These forces are absorbed by the ball bearings between the coupling sleeve 12 and the guide sleeve 110 and the bearing holder 130, in a low-friction manner, so that counter forces (i.e., frictional counter forces), which could reduce the driving torque, are minimized.

In the distribution, the display drum 70 is entrained by the rotation of the transmission sleeve 210 anticlockwise and is moved in the distal direction due to its engagement with the stationary mechanism holder 150, until it assumes its distal initial position. In this position, it is prevented from rotating further by a radial stop, whereby the distribution is terminated. After the end of the distribution, the display drum 70 indicates the dose "zero".

The distribution can be interrupted at any time by the push button 80 being released. Thereby, the couplings K3 and K2 couple again, and the coupling K1 uncouples again. The display drum 70 indicates the remaining residual dose which is further distributed when the push button is pressed again and thereby the distribution is continued.

The dose limiting ring 220 maintains its axial position during the distribution, because the transmission sleeve 210 and the coupling sleeve 120, between which the dose limiting ring 220 is situated, rotate synchronically.

After the end of the distribution, the injection device is ready for the next injection process. Compared with FIG. 16, however, two components have changed their position: On the one hand, the thrust sleeve 90 has travelled in accordance with the distributed dose in the distal direction. On the other hand, the dose limiting ring 220 has likewise travelled by an amount proportional thereto in the proximal direction. Apart from this, the state after the end of the injection corresponds to the initial state of FIG. 16. With each further injection, the thrust sleeve 90 therefore travels further in the distal direction, whereas the dose limiting ring 220 travels in the proximal direction. This is illustrated in FIG. 19, which illustrates the injection device after a first dose is administered, which corresponds to half the maximum individual dose, and then with the dosing sleeve a dose was again set, which in turn corresponds to half the maximum individual dose. The display drum indicates, as in FIG. 15, half the maximum individual dose, whereas the dose limiting ring 220 assumes a position in the transmission sleeve 210, which corresponds to the sum of the doses which have been set, e.g., twice half the maximum individual dose.

Figure 20:
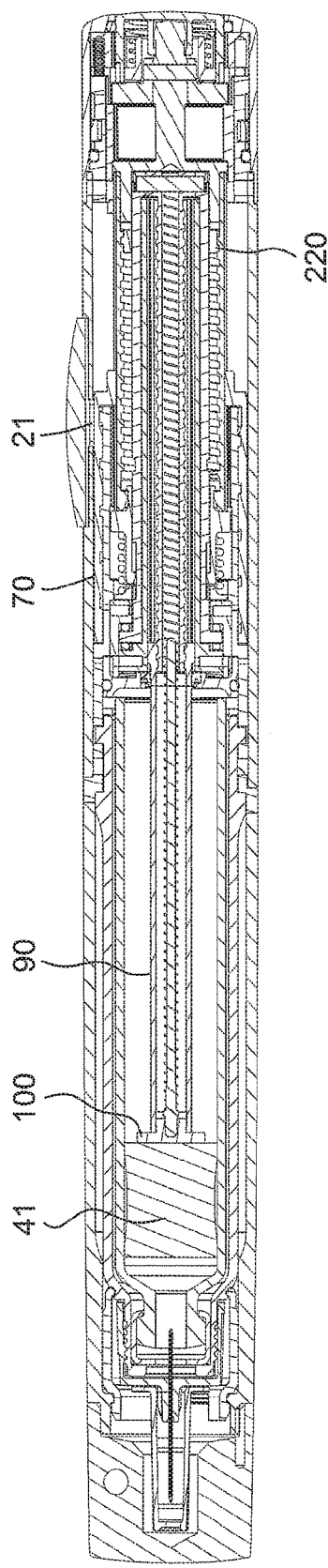
FIG. 20 is a longitudinal section through the injection device of FIG. 1A after a complete emptying of the carpule.

The maximum axial path by which the dose limiting ring 220 can travel in the proximal direction in the transmission sleeve corresponds to the content of a completely filled carpule. As soon as the sum of the doses set on the dosing sleeve corresponds to the carpule content, the dose limiting ring 220 reaches its proximal final position and abuts with its radial stop against the axial ring flange 235 of the coupling shaft 230, as is illustrated in FIG. 12A. Thereby, the dosing sleeve 60 is prevented from a further clockwise rotation, and no larger dose can be set than the dose corresponding to the remaining residual amount of the medicament in the carpule. FIG. 20 shows this situation, in which no further increasing of the dose is possible, although the display drum is situated in the distal initial position, i.e., the zero position. Correspondingly, the thrust sleeve 90 has reached its maximum, distal final position.

Tto exchange the carpule, the carpule sleeve 30 is detached from the mechanism holder 150 against the elastic resistance of the bayonet spring 170, and is unscrewed, guided through the corresponding guide slit 156 in the mechanism holder. Compulsorily, the bayonet sleeve 160 is twisted along its own, parallel guide slit 155, and is displaced in the distal direction. The guide sleeve 110 is drawn in the distal direction, and the movable parts, which are connected axially therewith, also travel in the distal direction, including the coupling sleeve 120, the threaded rod 190, the arresting sleeve 280, the transmission sleeve 210, the coupling shaft 230, the coupling disc 270 and the push button 80. The push button 80 is therefore drawn into the dosing sleeve 60 and thus indicates that the injection device is not ready for operation.

Through this axial displacement of the various parts of the mechanism, the couplings K2 and K3 come out of engagement, while K1 is already out of engagement. If a dose had still been set before the carpule change, but had not been administered, the wound spiral spring 310 sets the coupling shaft 230 and the transmission sleeve 210 connected therewith into an anticlockwise rotation, until the display drum 70 has reached its distal final position and prevents a further turning back by its radial stop on the mechanism holder 150. In this way, the display drum 70 is brought back into its distal initial position, the zero position. An automatic resetting of the dose display to zero therefore takes place.

If, before the carpule change, a residual amount of the medicament was still situated in the carpule 40, then the thrust sleeve 90 had not yet moved out to a maximum before the carpule change, and had therefore not yet reached its distal final position. On removal of the carpule sleeve 30, the helical spring 190 presses the guide needle 200, the thrust flange 100 and the thrust sleeve 90 in the distal direction. Thus, the threaded rod 180 is set in rotation via its screw connection with the interior of the thrust sleeve 90. The threaded rod 180 entrains the coupling sleeve 120 and the dose limiting ring 220. With this rotation, the dose limiting ring 220 is displaced into its proximal final position through its thread engagement with the transmission sleeve 210. As soon as the dose limiting ring 220 has reached this initial position, it prevents a further rotation of the coupling sleeve 120 and of the threaded rod 180, so that no further moving out of the thrust sleeve 90 is possible, and the thrust sleeve 90 has reached its distal final position, as illustrated in FIG. 1A. In addition, the display drum 70 is situated in the zero position, the dose limiting ring 220 in the proximal final position and the thrust sleeve 90 in its distal final position.

A new carpule 40 may be pushed into the carpule sleeve 30, and the carpule sleeve 30 with the carpule 40 held therein may be guided axially in the proximal direction against the housing sleeve 20. In this position, the stopper 41 of the carpule presses the thrust flange 100 and the thrust sleeve 90 against the force of the helical spring 190 in the proximal direction. As a result, the threaded rod 180 is set in rotation. The threaded rod entrains the coupling sleeve 120 and the dose limiting ring 220. The dose limiting ring, threadably engaged with the transmission sleeve 210, is displaced in the distal direction, i.e., in the direction of its initial position. The degree of displacement in this direction corresponds to the dose present in the carpule 40. With a completely filled carpule, the dose limiting ring 220 travels into its distal initial position. The carpule sleeve 30 is then pushed into the mechanism holder 150, with the radial pins 36 of the carpule sleeve 30 engaging again into the guide slits 156 in the mechanism holder 150 (cf. FIGS. 1 and 3). Through the positive guidance of the carpule sleeve 30 on insertion into the mechanism holder 150, the bayonet sleeve 160 is forced to follow the movement of the carpule sleeve 30 in the corresponding guide slits. The bayonet sleeve 160 is thereby brought back into its proximal final position, in which it is detachably locked by the bayonet disc 170 (cf. FIGS. 8 to 10). The injection device is thus situated in the initial position of FIG. 16 and, after the screwing of a new needle holder 31, is available for a new sequence of administrations.

Figure 21:
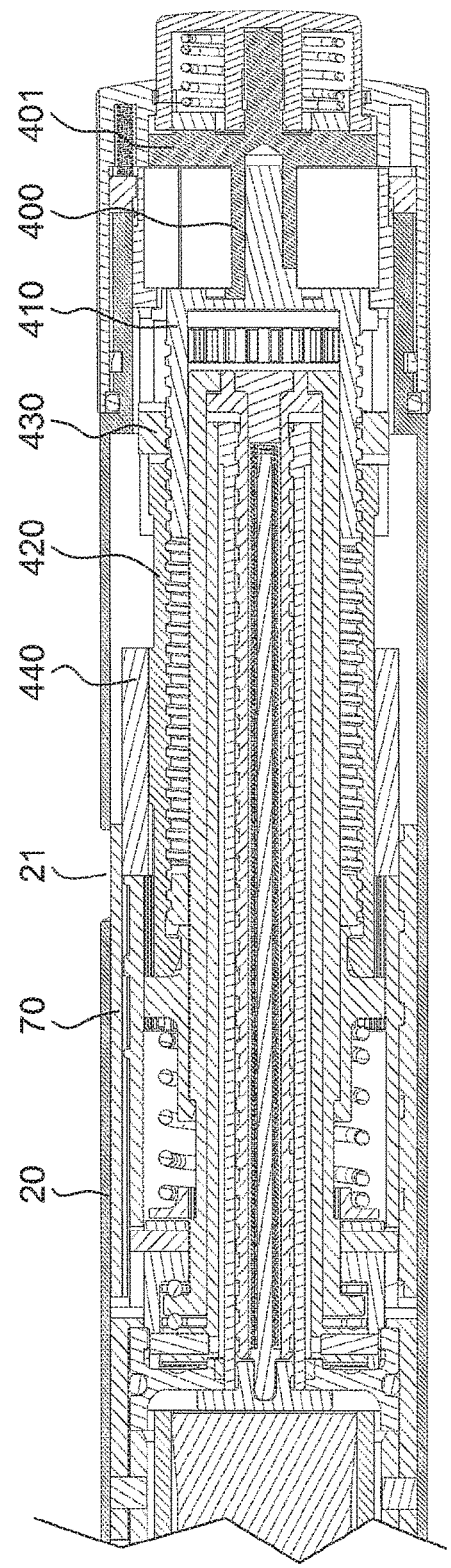
FIG. 21 is a longitudinal section through an injection device according to another embodiment.

In FIG. 21, another exemplary embodiment of an injection device according to the present invention is illustrated as a variant. The mode of operation is substantially the same as in the first embodiment described above. Parts which perform similarly are therefore designated by the same reference numbers as in the first embodiment, the differences of the second embodiment being described below.

In the second embodiment, the stop sleeve 240 is omitted. Rather, its function is taken over by the correspondingly extended housing sleeve 20.

The drive arrangement which, in the first embodiment, apart from the spiral spring 310, is formed from the coupling disc 270, coupling shaft 230 and transmission sleeve 210, is formed in the second embodiment by different parts, including a connecting shaft 400 (with coupling disc 401 formed integrally thereon), a first transmission sleeve 410 closed at the proximal end, and a second transmission sleeve 420 adjoining distally thereto. These three parts are, in turn, connected rigidly with each other.

Whereas in the first embodiment, the display drum served to indicate the set dose and to delimit the maximum individual dose which was able to be set in the dosing direction and to delimit the movement in the distribution direction, the latter function in the second embodiment is taken over by a second dose limiting ring 430. The latter is guided so as to be locked against relative rotation, but axially displaceable, in the housing sleeve 20. With an internal thread it runs on a corresponding external thread of the first transmission sleeve 410. Its axial movement is limited by two radial stops between a distal initial position, which corresponds to the zero position, and a proximal final position, which corresponds to the maximum dose which is able to be set. In this way, it takes over the stop functions of the display drum according to the first embodiment.

The display drum 70 in the second embodiment is guided axially displaceably via a carrier sleeve 440, rigidly connected therewith, and so as to be locked against relative rotation on the second transmission sleeve 420. Its mode of operation is otherwise identical to the first embodiment.

Apart from these differences, the structure and mode of operation of the injection device are substantially the same as in the first embodiment.

The differences between the first and the second embodiment show that the functions of an injection device according to the present invention can be reached in a variety of ways and the invention is in no way restricted to the examplary embodiments. Various further modifications are possible, which may be due to manufacturing requirements.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection pen for the administering of a fluid product from a reservoir having a dose limiting arrangement which allows the user to set as a maximum the remaining available residual dose of the reservoir, comprising:
   a transmission sleeve which sleeve at least partially surrounds a coupling sleeve and that rotates around a longitudinal axis of the pen;
   said coupling sleeve being coupled for rotation around the longitudinal axis of the pen during dose delivery;
   a dose limiter which is situated between the transmission sleeve and the coupling sleeve and which is threadedly engaged with the interior of the transmission sleeve and secured with regard to rotation on the coupling sleeve;
   such that during dose setting the dose limiter is axially displaced in the transmission sleeve via its threaded engagement with the transmission sleeve;
   and during dose delivery, the transmission sleeve, the dose limiter and the coupling sleeve rotate synchronically around the longitudinal axis of the pen and the dose limiter maintains its axial position relative to the coupling sleeve, whereby a thrust sleeve undergoes an axial displacement without rotation to inject the fluid product; and
   the maximum axial path by which the dose limiter can travel in the transmission sleeve corresponds to the content of a completely filled reservoir and as soon as the sum of the doses set corresponds to the content of a completely filled reservoir, the dose limiter reaches its final axial position and abuts with a stop on the transmission sleeve thereby preventing further increase in the dose setting.

2. An injection pen according to claim 1 wherein the transmission sleeve has an internal threading matching an external threading of the dose limiter.

3. An injection pen according to claim 1 wherein the coupling sleeve has at least one longitudinal rib for securing against axial rotation of the dose limiter relative to the coupling sleeve.

4. An injection pen according to claim 3 wherein the dose limiter is a dose limiting ring surrounding the coupling sleeve and having an external threading matching the internal threading of the transmission sleeve and longitudinal grooves on the inside to match the at least one longitudinal rib of the coupling sleeve.

5. An injection pen according to claim 1 wherein the coupling sleeve has a plurality of longitudinal ribs for securing against axial rotation of the dose limiter.

6. An injection pen according to claim 1 wherein the stop on the transmission sleeve preventing further increase in the dose setting is a radial stop.

7. An injection pen for the administering of a medicament from a reservoir having a dose limiting arrangement which allows the user to set as a maximum the remaining available residual dose of the reservoir, comprising:
   a first sleeve that at least partially surrounds a coupling sleeve and is rotatably mounted for rotational movement around a longitudinal axis of the pen;
   said coupling sleeve being coupled for rotation around the longitudinal axis of the pen during dose delivery;

a dose limiter which is situated on the inner side of the first sleeve and which is threadedly engaged with the interior of the first sleeve and secured with regard to rotation around the longitudinal axis on the coupling sleeve; and such that during dose setting the dose limiter is axially displaced in the first sleeve via its threaded engagement with the first sleeve, and during dose delivery, the first sleeve, the dose limiter and the coupling sleeve rotate synchronically around the longitudinal axis of the pen and the dose limiter maintains its axial position relative to the coupling sleeve, while a thrust sleeve is driven and undergoes an axial displacement without rotation to inject the medicament and the maximum axial path by which the dose limiter can travel in the first sleeve corresponds to the content of a completely filled reservoir and when the dose limiter reaches its final axial position and abuts with a stop on the first sleeve this prevents a larger dose from being set.

8. An injection pen according to claim 7 wherein the first sleeve has an internal threading corresponding to external threading of the dose limiter and the dose limiter at least partially surrounds the coupling sleeve.

9. An injection pen according to claim 7 wherein the coupling sleeve has at least one longitudinal rib for securing against axial rotation of the dose limiter relative to the coupling sleeve.

10. An injection pen according to claim 9 wherein the dose limiter is a dose limiting ring surrounding the coupling sleeve and having an external threading corresponding to the internal threading of the first sleeve and longitudinal grooves on the inside to match the at least one longitudinal rib of the coupling sleeve.

11. An injection pen according to claim 7 wherein the coupling sleeve has a plurality of longitudinal ribs for securing against axial rotation of the dose limiter.

12. An injection pen according to claim 7 wherein the stop on the first sleeve preventing further increase in the dose setting is a radial stop.

13. An injection pen according to claim 7 wherein the dose limiter is limited by at least one stop in its final position.

14. An injection pen according to claim 7 wherein the first sleeve is a cylindrical sleeve.

15. An injection pen according to claim 7, wherein the dose limiter reaches its final axial position as soon as the sum of the doses set corresponds to the content of a completely filled reservoir.

16. An injection pen for the administering of a medicament from a reservoir having a dose limiting arrangement which allows the user to set as a maximum the remaining available residual dose of the reservoir, comprising:

a first sleeve that at least partially surrounds a coupling sleeve and is rotatably mounted for rotational movement around a longitudinal axis of the pen;

said coupling sleeve being coupled for rotation around the longitudinal axis of the pen during dose delivery;

said dose limiting arrangement comprising a threaded element situated between the inner side of the first sleeve and the coupling sleeve which is threadedly engaged with the interior of the first sleeve and secured with regard to rotation around the longitudinal axis on the coupling sleeve, said threaded element further comprising a stop surface; and such that during dose setting the threaded element is axially displaced in the first sleeve via its threaded engagement with the first sleeve, and during dose delivery, the first sleeve, the threaded element and the coupling sleeve rotate synchronically around the longitudinal axis of the pen and the threaded element maintains its axial position relative to the coupling sleeve, while a thrust sleeve is driven and undergoes an axial displacement to inject the medicament and the maximum axial path by which the threaded element can travel in the first sleeve corresponds to the content of a completely filled reservoir and when the threaded element reaches its final axial position with its stop surface abutting with a corresponding counter surface on the first sleeve, this prevents a larger dose from being set.

17. An injection pen according to claim 16 wherein the first sleeve has an internal threading corresponding to external threading of the threaded element.

18. An injection pen according to claim 16 wherein the coupling sleeve has at least one longitudinal rib for securing against axial rotation of the threaded element relative to the coupling sleeve.

19. An injection pen according to claim 18 wherein the threaded element is a dose limiting ring surrounding the coupling sleeve and having an external threading corresponding to the internal threading of the first sleeve and longitudinal grooves on the inside to match the at least one longitudinal rib of the coupling sleeve.

20. An injection pen according to claim 16 wherein the stop preventing further increase in the dose setting is a radial stop.

* * * * *